(12) United States Patent
Wallace et al.

(10) Patent No.: US 10,517,624 B2
(45) Date of Patent: Dec. 31, 2019

(54) INVERTING THROMBECTOMY APPARATUSES AND METHODS

(71) Applicant: STRYKER CORPORATION, Fremont, CA (US)

(72) Inventors: Michael P. Wallace, Pleasanton, CA (US); E. Skott Greenhalgh, Gladwyne, PA (US)

(73) Assignee: Stryker Corporation, Fremont, CA (US)

( * ) Notice: Subject to any disclaimer, the term of this patent is extended or adjusted under 35 U.S.C. 154(b) by 85 days.

(21) Appl. No.: 15/611,546

(22) Filed: Jun. 1, 2017

(65) Prior Publication Data

US 2017/0348014 A1 Dec. 7, 2017

Related U.S. Application Data

(60) Provisional application No. 62/345,152, filed on Jun. 3, 2016.

(51) Int. Cl.
*A61B 17/221* (2006.01)
*A61B 17/22* (2006.01)
(Continued)

(52) U.S. Cl.
CPC ...... *A61B 17/221* (2013.01); *A61B 17/22031* (2013.01); *A61B 17/22032* (2013.01);
(Continued)

(58) Field of Classification Search
CPC . A61B 17/22; A61B 17/221; A61B 17/22031; A61B 2017/22034;
(Continued)

(56) References Cited

U.S. PATENT DOCUMENTS

| 4,222,380 A | 9/1980 | Terayama |
| 4,243,040 A | 1/1981 | Beecher |

(Continued)

FOREIGN PATENT DOCUMENTS

| AU | 2015210338 | 8/2015 |
| GB | 1588072 | 4/1981 |

(Continued)

OTHER PUBLICATIONS

PCT Invitation to Pay Additional Fees for International Appln. No. PCT/US2017/029345, Applicant Stryker Corporation, dated Oct. 17, 2017.

(Continued)

*Primary Examiner* — Katherine M Rodjom

(74) *Attorney, Agent, or Firm* — Vista IP Law Group LLP

(57) ABSTRACT

Rolling tractor tube mechanical thrombectomy apparatuses that may be deployed from out of a catheter in situ are described herein. These apparatuses may be delivered out of a catheter from a collapsed delivery configuration within the catheter to a deployed configuration out of the catheter, in which the same catheter is re-inserted between a tubular tractor and an elongate puller. In particular, any of these methods and apparatuses may be adapted to work with a tractor tube having an open end that is biased open, including using an annular bias.

26 Claims, 15 Drawing Sheets

(51) Int. Cl.
   *A61F 2/90* (2013.01)
   *A61B 17/00* (2006.01)
   *A61B 17/34* (2006.01)
   *A61F 2/82* (2013.01)

(52) U.S. Cl.
   CPC ...... *A61F 2/90* (2013.01); *A61B 2017/00349* (2013.01); *A61B 2017/00778* (2013.01); *A61B 2017/00867* (2013.01); *A61B 2017/2215* (2013.01); *A61B 2017/22038* (2013.01); *A61B 2017/3435* (2013.01); *A61F 2002/825* (2013.01); *A61F 2230/0056* (2013.01)

(58) Field of Classification Search
   CPC ........... A61B 2017/22035; A61B 2017/22079; A61B 2017/2215; A61B 1/00151; A61B 1/3435; A61B 2017/00778; A61B 2017/00867; A61B 2017/3435
   See application file for complete search history.

(56) References Cited

U.S. PATENT DOCUMENTS

| | | | |
|---|---|---|---|
| 4,324,262 A | 4/1982 | Hall | |
| 4,469,100 A | 9/1984 | Hardwick | |
| 4,604,094 A | 8/1986 | Shook | |
| 4,646,736 A | 3/1987 | Auth | |
| 4,863,440 A | 9/1989 | Chin | |
| 4,946,440 A | 8/1990 | Hall | |
| 5,364,345 A | 11/1994 | Lowery et al. | |
| 5,389,100 A | 2/1995 | Bacich et al. | |
| 5,662,703 A | 9/1997 | Yurek et al. | |
| 5,971,938 A | 10/1999 | Hart et al. | |
| 6,221,006 B1 | 4/2001 | Dubrul et al. | |
| 6,238,412 B1 | 5/2001 | Dubrul et al. | |
| 6,245,078 B1 | 6/2001 | Ouchi | |
| 6,258,115 B1 | 7/2001 | Dubrul | |
| 6,544,278 B1 | 4/2003 | Vrba et al. | |
| 6,569,181 B1 | 5/2003 | Burns | |
| 6,620,179 B2 | 9/2003 | Brook et al. | |
| 6,635,068 B1 | 10/2003 | Dubrul et al. | |
| 6,830,561 B2 | 12/2004 | Jansen et al. | |
| 6,846,029 B1 | 1/2005 | Ragner et al. | |
| 6,942,682 B2 | 9/2005 | Vrba et al. | |
| 7,621,870 B2 | 11/2009 | Berrada et al. | |
| 7,780,696 B2* | 8/2010 | Daniel ................. | A61B 17/221 606/200 |
| 8,092,486 B2 | 1/2012 | Berrada et al. | |
| 8,657,867 B2 | 2/2014 | Dorn et al. | |
| 8,721,714 B2 | 5/2014 | Kelley | |
| 8,784,442 B2 | 7/2014 | Jones et al. | |
| 8,795,305 B2 | 8/2014 | Martin et al. | |
| 8,956,384 B2 | 2/2015 | Berrada et al. | |
| 9,028,401 B1 | 5/2015 | Bacich et al. | |
| 9,125,683 B2 | 9/2015 | Farhangnia et al. | |
| 9,155,552 B2 | 10/2015 | Ulm, III | |
| 9,173,668 B2 | 11/2015 | Ulm, III | |
| 9,186,487 B2 | 11/2015 | Dubrul et al. | |
| 9,358,037 B2 | 1/2016 | Farhangnia et al. | |
| 9,351,747 B2 | 5/2016 | Kugler et al. | |
| 9,463,035 B1 | 10/2016 | Greenhalgh et al. | |
| 9,717,514 B2 | 8/2017 | Martin et al. | |
| 9,848,975 B2 | 12/2017 | Hauser | |
| 9,849,014 B2 | 12/2017 | Kusleika | |
| 9,962,178 B2 | 5/2018 | Greenhalgh et al. | |
| 1,001,033 A1 | 7/2018 | Greenhalgh et al. | |
| 1,002,875 A1 | 7/2018 | Wallace et al. | |
| 10,016,266 B2 | 7/2018 | Hauser | |
| 10,130,385 B2 | 11/2018 | Farhangnia et al. | |
| 10,271,864 B2 | 4/2019 | Greenhalgh et al. | |
| 2002/0032455 A1 | 3/2002 | Boock et al. | |
| 2002/0173819 A1 | 11/2002 | Leeflang et al. | |
| 2003/0083693 A1 | 5/2003 | Daniel et al. | |
| 2003/0135258 A1 | 7/2003 | Andreas et al. | |
| 2003/0153873 A1 | 8/2003 | Luther et al. | |
| 2003/0176884 A1 | 9/2003 | Berrada et al. | |
| 2003/0208224 A1 | 11/2003 | Broome | |
| 2004/0098033 A1 | 5/2004 | Leeflang et al. | |
| 2005/0085826 A1 | 4/2005 | Nair et al. | |
| 2005/0085849 A1 | 4/2005 | Sepetka et al. | |
| 2005/0119668 A1 | 6/2005 | Teague et al. | |
| 2005/0177132 A1 | 8/2005 | Lentz et al. | |
| 2005/0187570 A1 | 8/2005 | Nguyen et al. | |
| 2005/0283166 A1 | 12/2005 | Greenhalgh | |
| 2005/0283186 A1 | 12/2005 | Berrada et al. | |
| 2006/0042786 A1 | 3/2006 | West | |
| 2006/0089533 A1 | 4/2006 | Ziegler et al. | |
| 2006/0173525 A1 | 8/2006 | Behl et al. | |
| 2006/0195137 A1 | 8/2006 | Sepetka et al. | |
| 2006/0200221 A1 | 9/2006 | Malewicz | |
| 2006/0293696 A1 | 12/2006 | Fahey et al. | |
| 2007/0112374 A1 | 5/2007 | Paul, Jr. et al. | |
| 2007/0149996 A1 | 6/2007 | Coughlin | |
| 2007/0213765 A1 | 9/2007 | Adams et al. | |
| 2010/0030256 A1 | 2/2010 | Dubrul et al. | |
| 2010/0042136 A1 | 2/2010 | Berrada et al. | |
| 2010/0087844 A1 | 4/2010 | Fischer, Jr. | |
| 2010/0137846 A1 | 6/2010 | Desai et al. | |
| 2010/0190156 A1 | 7/2010 | Van Wordragen et al. | |
| 2010/0249815 A1 | 9/2010 | Jantzen et al. | |
| 2011/0034987 A1 | 2/2011 | Kennedy | |
| 2011/0118817 A1 | 5/2011 | Gunderson et al. | |
| 2011/0160763 A1 | 6/2011 | Ferrera et al. | |
| 2011/0265681 A1 | 11/2011 | Allen et al. | |
| 2011/0288529 A1 | 11/2011 | Fulton | |
| 2011/0288572 A1 | 11/2011 | Martin | |
| 2012/0083824 A1 | 4/2012 | Berrada et al. | |
| 2012/0083868 A1 | 4/2012 | Shrivastava | |
| 2012/0271105 A1 | 10/2012 | Nakamura et al. | |
| 2013/0046332 A1 | 2/2013 | Jones et al. | |
| 2013/0096571 A1 | 4/2013 | Massicotte et al. | |
| 2013/0116721 A1 | 5/2013 | Takagi et al. | |
| 2013/0226196 A1 | 8/2013 | Smith | |
| 2013/0317589 A1 | 11/2013 | Martin et al. | |
| 2013/0345739 A1 | 12/2013 | Brady et al. | |
| 2014/0005712 A1 | 1/2014 | Martin et al. | |
| 2014/0046133 A1 | 2/2014 | Nakamura et al. | |
| 2014/0155980 A1 | 6/2014 | Turjman | |
| 2014/0257253 A1 | 9/2014 | Jemison | |
| 2014/0276403 A1 | 9/2014 | Follmer et al. | |
| 2014/0330286 A1 | 11/2014 | Wallace | |
| 2014/0336691 A1 | 11/2014 | Jones et al. | |
| 2014/0364896 A1 | 12/2014 | Consigny | |
| 2014/0371779 A1 | 12/2014 | Vale et al. | |
| 2015/0005781 A1* | 1/2015 | Lund-Clausen ..... | A61B 17/221 606/127 |
| 2015/0018859 A1 | 1/2015 | Quick et al. | |
| 2015/0018860 A1 | 1/2015 | Quick et al. | |
| 2015/0088190 A1 | 3/2015 | Jensen | |
| 2015/0164523 A1 | 6/2015 | Brady et al. | |
| 2015/0164666 A1 | 6/2015 | Johnson et al. | |
| 2015/0190155 A1 | 7/2015 | Ulm, III | |
| 2015/0190156 A1 | 7/2015 | Ulm, III | |
| 2015/0196380 A1 | 7/2015 | Berrada et al. | |
| 2016/0022293 A1 | 1/2016 | Dubrul et al. | |
| 2016/0074627 A1 | 3/2016 | Cottone | |
| 2016/0106448 A1 | 4/2016 | Brady et al. | |
| 2016/0106449 A1 | 4/2016 | Brady et al. | |
| 2016/0113663 A1 | 4/2016 | Brady et al. | |
| 2016/0113664 A1 | 4/2016 | Brady et al. | |
| 2016/0113665 A1 | 4/2016 | Brady et al. | |
| 2017/0112513 A1 | 4/2017 | Marchand et al. | |
| 2017/0303939 A1 | 10/2017 | Greenhalgh et al. | |
| 2017/0303942 A1 | 10/2017 | Greenhalgh et al. | |
| 2017/0303947 A1 | 10/2017 | Greenhalgh et al. | |
| 2017/0303948 A1 | 10/2017 | Wallace et al. | |
| 2017/0348014 A1 | 12/2017 | Wallace et al. | |
| 2018/0042624 A1 | 2/2018 | Greenhalgh et al. | |
| 2018/0042626 A1 | 2/2018 | Greenhalgh et al. | |
| 2018/0070968 A1 | 3/2018 | Wallace et al. | |
| 2019/0117244 A1 | 4/2019 | Wallace et al. | |
| 2019/0133622 A1 | 5/2019 | Wallace et al. | |
| 2019/0133623 A1 | 5/2019 | Wallace et al. | |
| 2019/0133624 A1 | 5/2019 | Wallace et al. | |

(56) References Cited

U.S. PATENT DOCUMENTS

| | | |
|---|---|---|
| 2019/0133625 A1 | 5/2019 | Wallace et al. |
| 2019/0133626 A1 | 5/2019 | Wallace et al. |
| 2019/0133627 A1 | 5/2019 | Wallace et al. |

FOREIGN PATENT DOCUMENTS

| | | |
|---|---|---|
| GB | 2498349 | 7/2013 |
| WO | WO 00/32118 | 6/2000 |
| WO | WO 2009086482 | 7/2009 |
| WO | WO 2012/009675 | 1/2012 |
| WO | WO 2012/049652 | 4/2012 |
| WO | WO 2012162437 | 11/2012 |
| WO | WO 2017/058280 | 4/2017 |
| WO | WO2017189535 | 11/2017 |
| WO | WO2017189550 | 11/2017 |
| WO | WO2017189591 | 11/2017 |
| WO | WO2017189615 | 11/2017 |
| WO | WO 2017210487 | 12/2017 |
| WO | WO 2018049317 | 3/2018 |
| WO | WO 2019010318 | 1/2019 |
| WO | WO 2019094456 | 5/2019 |

OTHER PUBLICATIONS

Non-Final Office Action for U.S. Appl. No. 15/496,786, dated Nov. 1, 2017.
PCT International Search Report and Written Opinion for International Appln. No. PCT/US2017/050933, Applicant Stryker Corporation, forms PCT/ISA/210, 220, and 237, dated Nov. 10, 2017 (16 pages).
Response to Non-Final Office Action for U.S. Appl. No. 14/496,786, filed Feb. 1, 2018.
Non-final office action dated Feb. 1, 2018 for U.S. Appl. No. 15/496,668.
This Application is related to U.S. Appl. No. 15/496,570, U.S. Appl. No. 15/496,668, U.S. Appl. No. 15/496,786, U.S. Appl. No. 15/497,092, U.S. Appl. No. 15/291,015, U.S. Appl. No. 15/700,685, U.S. Appl. No. 15/795,097, and U.S. Appl. No. 15/794,939.
Response to Restriction for U.S. Appl. No. 15/496,668, filed Feb. 21, 2018.
International search report and written opinion dated Feb. 28, 2018 for PCT/US2017/029345, Applicant Stryker Corporation 26 pages.
Notice of Allowance dated Mar. 22, 2018 for U.S. Appl. No. 15/496,668.
Notice of Allowance dated Apr. 19, 2018 for U.S. Appl. No. 15/496,570.
Notice of Allowance dated Apr. 19, 2018 for U.S. Appl. No. 15/496,786.
Non-Final Office Action dated Sep. 5, 2018 for U.S. Appl. No. 15/291,015.
Extended European Search Report dated Aug. 22, 2018 for European patent appln No. 16852212.6.
Extended European Search Report dated Oct. 5, 2018 for European patent appln No. 18174891.4.
Invitation to Pay Additional Fees for International Patent Appln. No. PCT/US2018/040937 dated Sep. 26, 2018.
Response to Non-Final Office Action for U.S. Appl. No. 15/291,015, filed Sep. 5, 2018.
International search report and written opinion dated Nov. 14, 2018 for PCT/US2018/040937, Applicant Stryker Corporation 16 pages.
Notice of Allowance dated Dec. 11, 2018 for U.S. Appl. No. 15/291,015.
This Application is related to U.S. Appl. No. 15/496,570, U.S. Appl. No. 15/496,668, U.S. Appl. No. 15/496,786, U.S. Appl. No. 15/497,092, U.S. Appl. No. 15/291,015, and U.S. Appl. No. 15/700,685.
Non-Final Office Action for U.S. Appl. No. 15/496,570, dated Aug. 9, 2017.
PCT International Search Report and Written Opinion for International Appln. No. PCT/US2017/029440, Applicant Stryker Corporation, dated Jul. 7, 2017.
PCT Invitation to Pay Additional Fees for International Appln. No. PCT/US2017/029366, Applicant Stryker Corporation, dated Jul. 7, 2017.
PCT International Search Report and Written Opinion for International Appln. No. PCT/US2017/029472, Applicant Stryker Corporation, dated Jul. 7, 2017.
PCT International Search Report and Written Opinion for International Appln. No. PCT/US2017/035543, Applicant Stryker Corporation, dated Aug. 14, 2017.
PCT International Search Report and Written Opinion for International Appln. No. PCT/US2017/029366, Applicant Stryker Corporation, dated Aug. 29, 2017.
Invitation to Pay Additional Fees for International Patent Appln. No. PCT/US2018/059607 dated Jan. 31, 2019.
Japanese Office action dated Mar. 19, 2019 for Japanese Application No. 2018-535810 (with English Language translation).
International Search Report and Written Opinion dated Mar. 28, 2019 for International Appln. No. PCT/US2018/059607.
Response to Extended European Search Report for EP Patent Appln. No. 16852212.6 dated Mar. 15, 2019.
European Patent Office Communication Rule 161(1) and 162 dated Feb. 5, 2019 for EP Patent Appln. No. 17729703.3.
European Patent Office Communication Rule 161(1) and 162 EPC for EP Patent Appln. No. 17737084.8 dated Dec. 18, 2018.
European Patent Office Communication Rule 161(1) and 162 for EP Patent Appln. No. 17722277.5 dated Dec. 13, 2018.
European Patent Office Communication Rule161(1) and 162 dated Dec. 13, 2018 for EP Patent Appln. No. 17722290.8.
European Patent Office Communication Rule 161(1) and 162 dated Dec. 13, 2018 for EP Patent Appln. No. 17721036.6.
Response to Extended European Search Report for EP Patent Appln. No. 18174891.4 dated May 28, 2019.
Restriction Requirement dated Jun. 28, 2019 for U.S. Appl. No. 15/700,685.
International Search Report and Written Opinion dated May 6, 2016 for PCT/US2016/017982.
Response to European Patent Office Communication Rule 161(1) and 162 EPC filed Jun. 11, 2019, for EP Patent Appln. No. 17737084.8.
Response to European Patent Office Communication Rule 161(1) and 162 dated Jun. 4, 2019 for EP Patent Appln. No. 17722277.5.
Response to European Patent Office Communication Rule161(1) and 162 dated Jun. 4, 2019 for EP Patent Appln. No. 17722290.8.
Response to European Patent Office Communication 161(1) and 162 dated Jun. 11, 2019 for EP Patent Appln. No. 17721036.6.
European Patent Office Communication Rule161(1) and 162 dated Apr. 23, 2019 for EP Patent Appln. No. 17772186.7.
Response to Non-Final Office Action dated Nov. 8, 2017 for U.S. Appl. No. 15/496,570.
Response to Non-Final Office Action dated Feb. 1, 2018 for U.S. Appl. No. 15/496,786.
Restriction Requirement dated Apr. 11, 2019 for U.S. Appl. No. 15/497,092.
Response to Restriction Requirement dated Jun. 11, 2019 for U.S. Appl. No. 15/497,092.
Ex Parte Quayle office action dated Jul. 16, 2019 for U.S. Appl. No. 15/497,092.
Response to Rule 161(1) and 162 EPC filed on Jul. 23, 2019 for EP application No. 17729703.3.
PCT International Search Report and Written Opinion for International Patent Appln. No. PCT/US2019/032601 Applicant Stryker Corporation, dated Jul. 23, 2019 (12 pages).
Response to Restriction Requirement dated Jul. 25, 2019 for U.S. Appl. No. 15/700,685.
Response to Ex Parte Quayle office action filed Jul. 25, 2019 for U.S. Appl. No. 15/497,092.
Office action dated Jun. 5, 2019 for Chinese application No. 2019053101871820, including partial English language translation provided by the foreign associate.
Wikipedia; Embolectomy; retrieved from the internet: https://en.wikipedia.org/wiki/Embolectomy; 4 pgs.; retrieved/printed: Mar. 24, 2016.

(56) References Cited

OTHER PUBLICATIONS

O'Sullivan; Thrombolysis versus thrombectomy in acute deep vein thrombosis; Interventional Cardiology; 3(5); pp. 589-596; Oct. 2011.
Capture Vascular Systems; (company website); retrieved from the internet: http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/20150228193218/http://wvvvv.edwards.com/products/vascular/atraumaticocclusion/pages/occlusioncatheter.aspx; ©2011; 2 pgs.; retrieved/printed: Mar. 24, 2011.
Boston Scientific; Fetch(TM) 2 Aspiration Catheter (product information); retrieved from the internet: http://www.bostonscientific.com/en-US/products/thrombectomy-systems/fetch2-aspiration-catheter.html; 5 pgs.; retrieved/printed: Mar. 24, 2016.
Penumbra, Inc.; Indigo® System (product information); retrieved from the internet: http://www.penumbrainc.com/peripherallpercutaneous-thromboembolectomy/indigo-system; 2 pgs.; retrieved/printed: Mar. 24, 2016.
Youtube; Merci Retrieval System X Series Animation; uploaded Mar. 16, 2009 (product information); retrieved from the internet: https://www.youtube.com/watch?v=MGX7deuFkhc; 3 pgs.; retrieved/printed: Mar. 24, 2016.
Covidien; Solitaire(TM) AS Neurovascular Remodeling Device (product information); retrieved from the internet: http://www.ev3.net/neuro/intl/remodeling-devices/solitaire-ab.htm; ©2015; 2 pgs.; retrieved/printed: Mar. 24, 2016.
Notice of Allowance for U.S. Appl. No. 15/043,996 dated Jun. 9, 2016.
Ex Parte Quayle office action dated Aug. 2, 2019 for U.S. Appl. No. 15/497,092.
Non Final Office Action dated Aug. 23, 2019 for U.S. Appl. No. 15/700,685.
Non Final Office Action dated Sep. 3, 2019 for U.S. Appl. No. 15/794,939.
Rule 71(3) Allowance for EP Patent Appln. No. 18174891.4 dated Jul. 30, 2019.
Response to Ex Parte Quayle office action filed Sep. 17, 2019 for U.S. Appl. No. 15/497,092.
Office action response filed on Sep. 26, 2019 for Chinese Patent Application No. 2016800567527, no translation received.
Non-Final Office Action dated Oct. 4, 2019 for U.S. Appl. No. 15/795,097.
Response to Restriction filed Oct. 4, 2019 for U.S. Appl. No. 15/795,097.
Notice of Allowance dated Sep. 27, 2019 for U.S. Appl. No. 15/497,092.
Extended European Search Report dated Oct. 8, 2019 for European Patent Application No. 19191925.7.
Office action dated Oct. 7, 2019 for European Patent Application No. 17729703.3.
Office action dated Oct. 7, 2019 for European Patent Application No. 17737084.8.
Response to European Patent Office Communication Rule161(1) and 162 filed Oct. 17, 2019 for EP Patent Appln. No. 17772186.7.
Invitation to Pay Additional Fees for International Patent Appln. No. PCT/US2019/050467 dated Oct. 25, 2019.
International Search Report and Written Opinion for International Patent Appln. No. PCT/US2019/050410 dated Oct. 25, 2019.

* cited by examiner

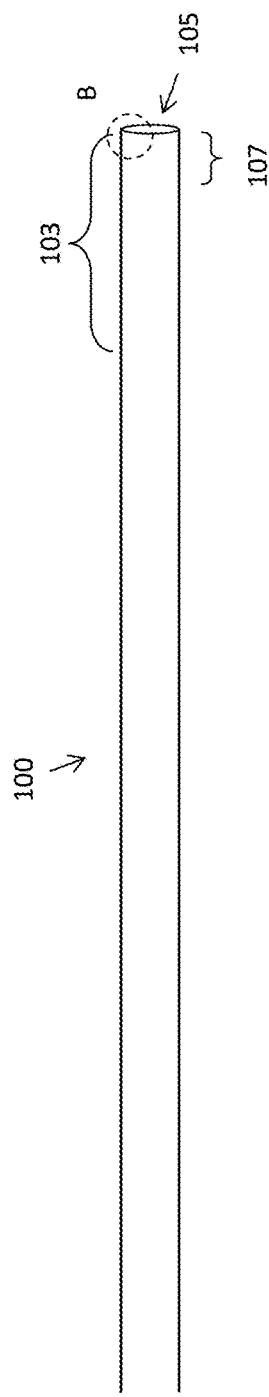
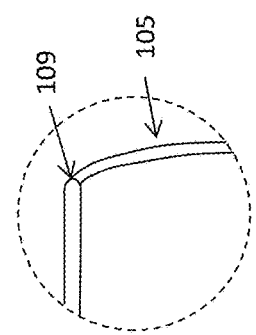
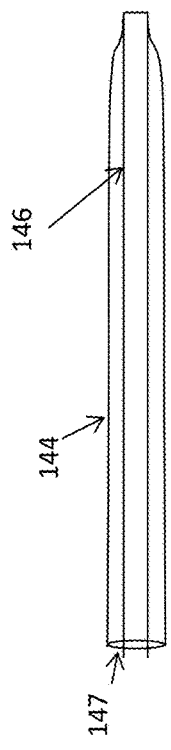
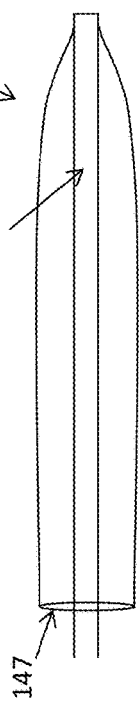
FIG. 1A
FIG. 1B
FIG. 1C
FIG. 1D

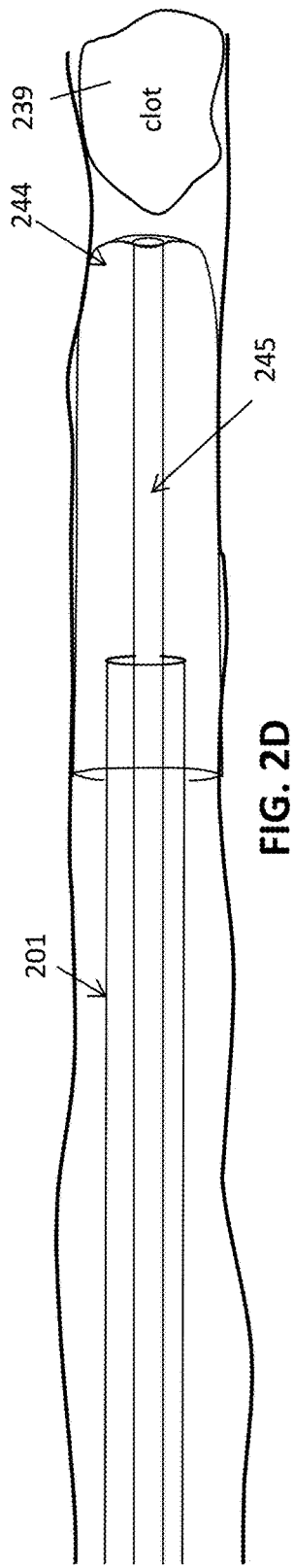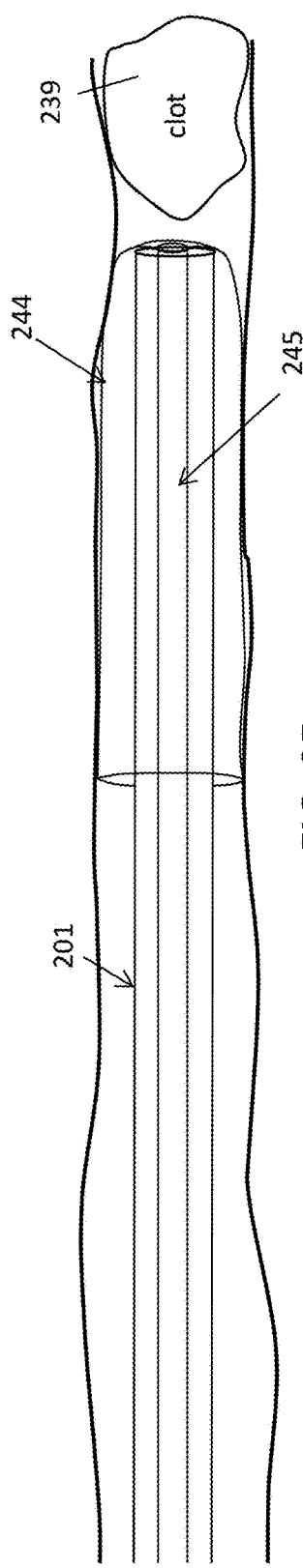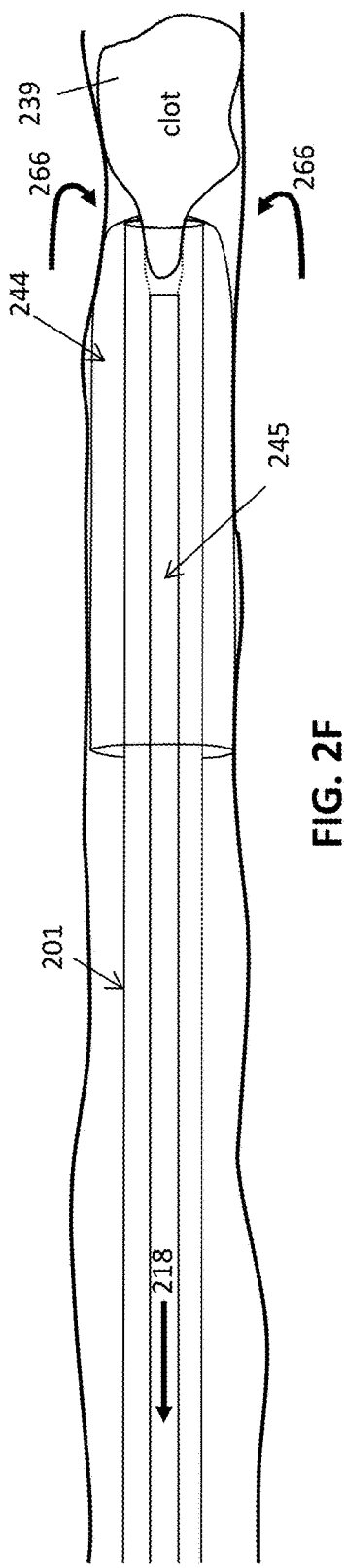

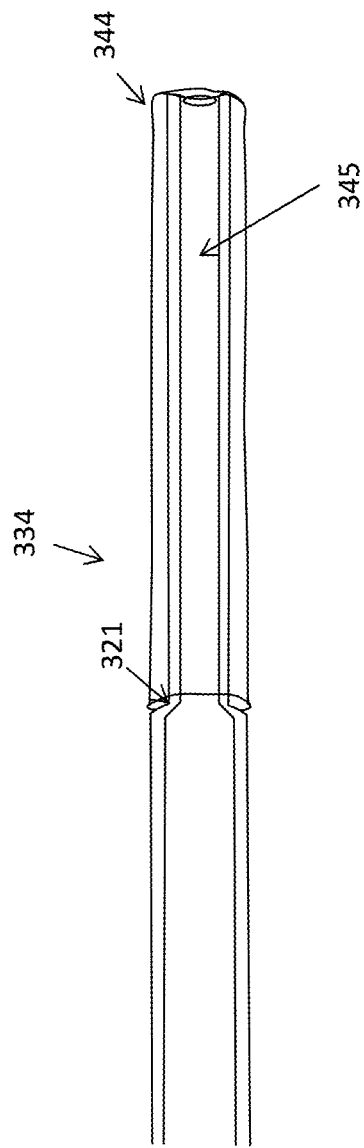
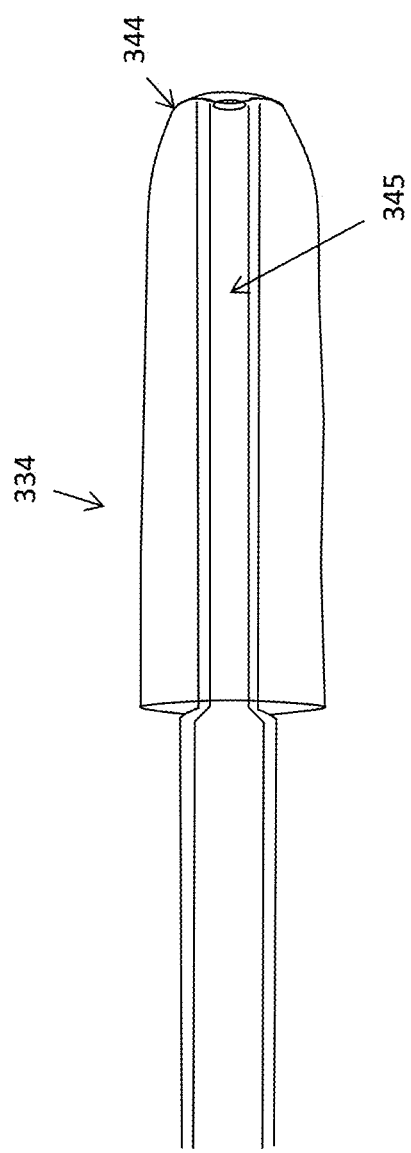
FIG. 3A
FIG. 3B

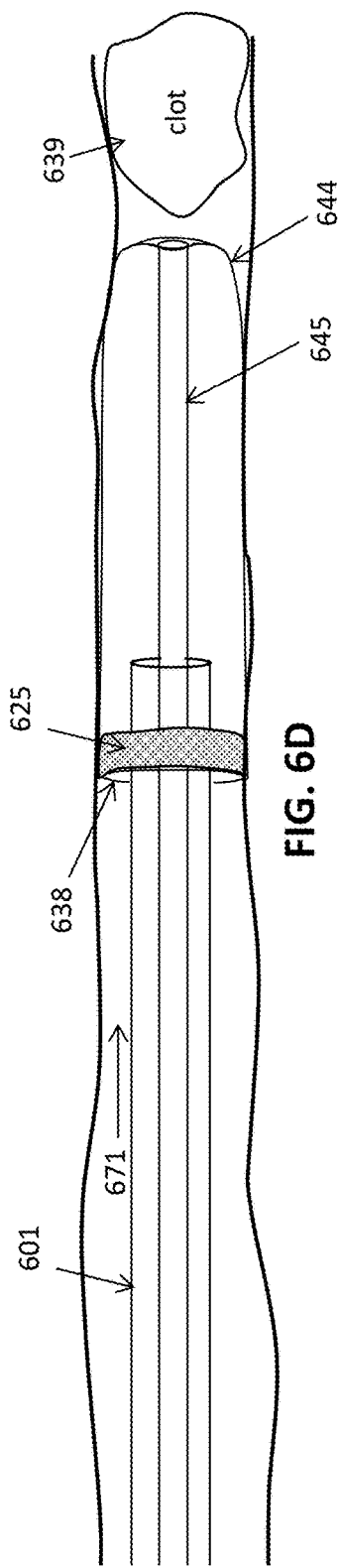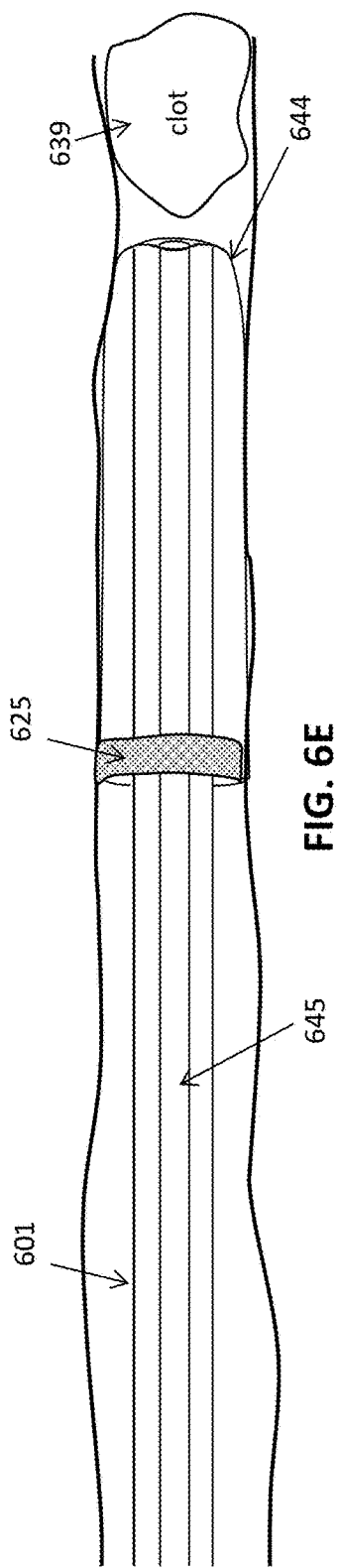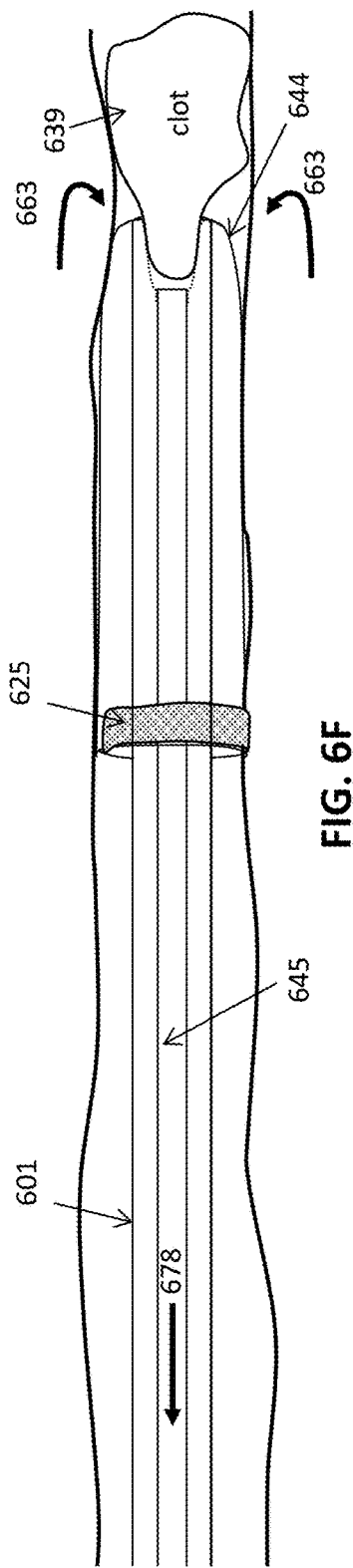

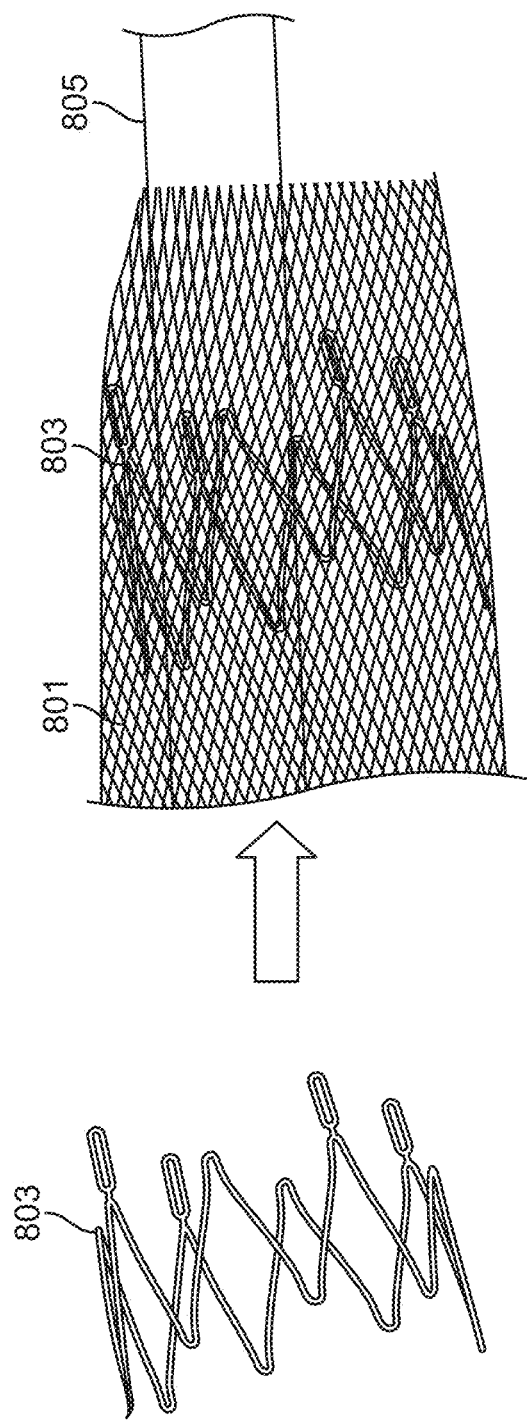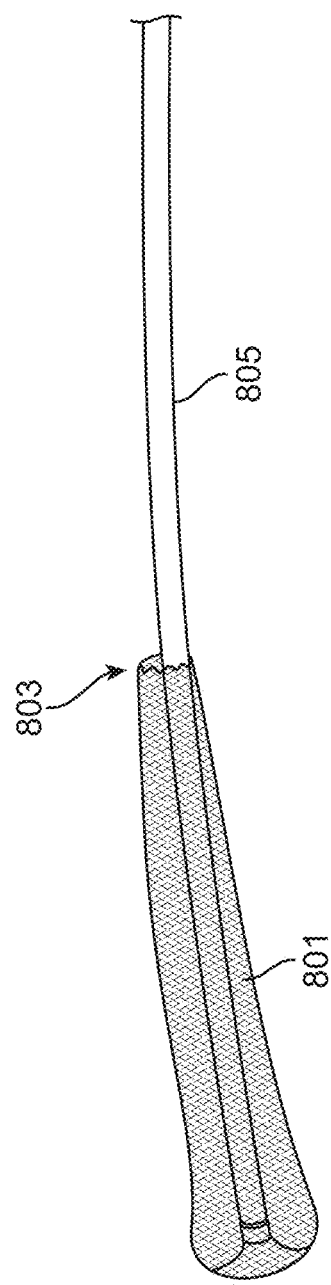

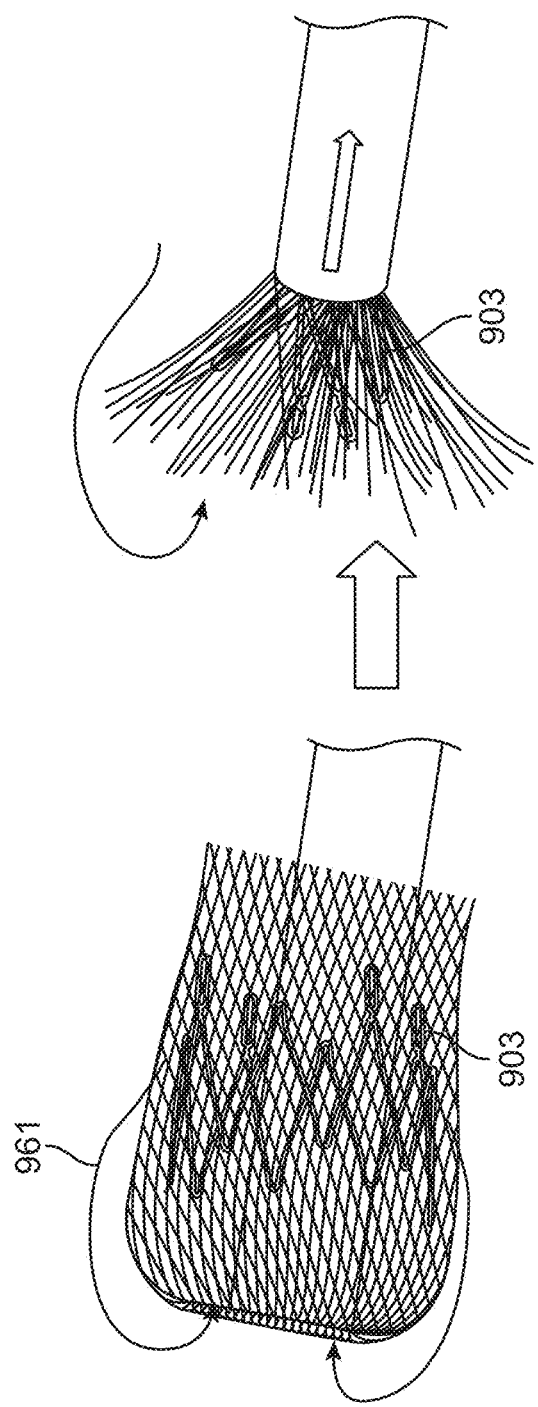
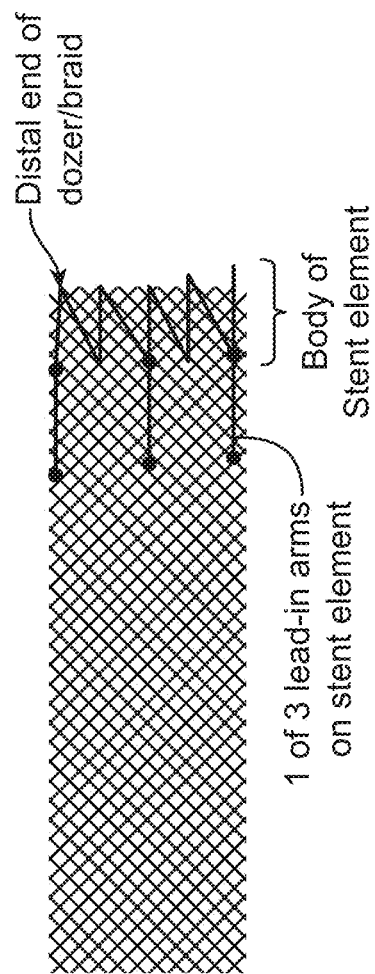
FIG. 9A
FIG. 9B
FIG. 9C

INVERTING THROMBECTOMY APPARATUSES AND METHODS

CROSS REFERENCE TO RELATED APPLICATIONS

This patent application claims priority to U.S. provisional patent application No. 62/345,152, filed on Jun. 3, 2016, and titled "DOZER THROMBECTOMY SYSTEM 2".

This patent application may be related to U.S. patent application Ser. No. 15/291,015, filed on Oct. 11, 2016, titled "MECHANICAL THROMBECTOMY APPARATUSES AND METHODS", which is a continuation of U.S. patent application Ser. No. 15/043,996, filed Feb. 15, 2016, now U.S. Pat. No. 9,463,035, which claims priority to each of the following provisional patent applications: U.S. Provisional Patent Application No. 62/284,300, filed Sep. 28, 2015; U.S. Provisional Patent Application No. 62/284,752, filed Oct. 8, 2015; and U.S. Provisional Patent Application No. 62/245,560, filed Oct. 23, 2015.

Each of these patents and patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein relate to mechanical removal of objects from within a body. In particular, described herein are mechanical thrombectomy apparatuses and methods.

BACKGROUND

Many vascular problems stem from insufficient blood flow through blood vessels. One causes of insufficient or irregular blood flow is a blockage within a blood vessel referred to as a blood clot, or thrombus. Thrombi can occur for many reasons, including after a trauma such as surgery, or due to other causes. For example, a large percentage of the more than 1.2 million heart attacks in the United States are caused by blood clots (thrombi) which form within a coronary artery. It is often desirable to remove tissue from the body in a minimally invasive manner as possible, so as not to damage other tissues. For example, removal of tissue, such as blood clots, from within a patient's vasculature may improve patient conditions and quality of life.

When a thrombus forms, it may effectively stop the flow of blood through the zone of formation. If the thrombus extends across the interior diameter of an artery, it may cut off the flow of blood through the artery. If one of the coronary arteries is 100% thrombosed, the flow of blood is stopped in that artery, resulting in a shortage of oxygen carrying red blood cells, e.g., to supply the muscle (myocardium) of the heart wall. Such a thrombosis is unnecessary to prevent loss of blood but can be undesirably triggered within an artery by damage to the arterial wall from atherosclerotic disease. Thus, the underlying disease of atherosclerosis may not cause acute oxygen deficiency (ischemia) but can trigger acute ischemia via induced thrombosis. Similarly, thrombosis of one of the carotid arteries can lead to stroke because of insufficient oxygen supply to vital nerve centers in the cranium. Oxygen deficiency reduces or prohibits muscular activity, can cause chest pain (angina pectoris), and can lead to death of myocardium which permanently disables the heart to some extent. If the myocardial cell death is extensive, the heart will be unable to pump sufficient blood to supply the body's life sustaining needs. The extent of ischemia is affected by many factors, including the existence of collateral blood vessels and flow which can provide the necessary oxygen.

Clinical data indicates that clot removal may be beneficial or even necessary to improve outcomes. For example, in the peripheral vasculature, inventions and procedures can reduce the need for an amputation by 80 percent. The ultimate goal of any modality to treat these conditions of the arterial or venous system is to remove the blockage or restore patency, quickly, safely, and cost effectively. This may be achieved by thrombus dissolution, fragmentation, thrombus aspiration or a combination of these methods.

Mechanical thrombectomy devices may be particularly advantageous. Depending on the size, location and extent of a clot, it may also be particularly advantageous to mechanical retrieve and break apart the clot in a manner that is both safe and effective. There is a definite need for a thrombectomy device, and particularly a mechanical thrombectomy device that can be more effective in removing tissue such as clots from within a body. Described herein are apparatuses (devices, systems and kit) and methods of using them that may address the needs and problems discussed above.

SUMMARY OF THE DISCLOSURE

Described herein are mechanical thrombectomy apparatuses (devices, systems, etc.) and methods of using and making them. These apparatuses may be configured for reliable operation in particular in narrow regions of the body, including peripheral vascular and neurovascular regions. Typically, the mechanical thrombectomy apparatuses described herein are inverting tractor thrombectomy apparatuses that includes a tractor (e.g., tractor region, tractor portion, etc.) comprising a flexible tube of material that inverts over itself as it rolls over a distal end opening of an elongate inversion support. The elongate inversion support typically comprises a catheter having a distal end opening into which the tractor inverts. The flexible tractor inverts and rolls back into itself and may be drawn into the elongate inversion support in a conveyor-like motion; the outward-facing region rolls around to become an inward-facing region, e.g., within the lumen of the elongate inversion support. The rolling motion may thus draw a clot or other object within a vessel into the elongate inversion support.

The apparatus may be deployed from a collapsed configuration using an in situ deployment, wherein the tractor is folded over an elongate puller/pusher member (which may be a hollow tube, wire or the like), and is collapsed down into a compact form for positioning within the vessel. Once the distal end of the tractor is in position within the vessel, the tractor may be expanded open and the distal end of the catheter over which the tractor is to be rolled or inverted is advanced distally between the tractor and the puller/pusher member, so the distal end opening of the catheter is positioned distally and the tractor can roll over the distal end and invert when the puller/pusher is pulled proximally.

In practice, it is beneficial to provide a tractor that is able to be radially compacted to a large degree (e.g., to less than 0.7× the diameter, 0.6× the diameter, 0.5× the diameter, 0.4× the diameter, 0.3× the diameter 0.2× the diameter, 0.1× the diameter, etc.) while still maintaining high degree of flexibility for ease in rolling and inverting over the distal end. Further, the tractor may be advantageously biased so that it has an outer diameter when collapsed into the catheter (after being rolled and inverted into the catheter) that is greater than 0.7× the inner diameter of the catheter (e.g., greater than 0.7×, 0.75×, 0.8×, 0.85×, 0.9×, 0.95×, etc.). In some variations, it may be particularly beneficial if the outer diameter of the portion of the tractor that extends along the outer diameter of the catheter is biased to have an inner diameter that is between 1.1× and 2× the outer diameter of the catheter (e.g., between 1.1× and 1.9×, between 1.1× and 1.8×, between 1.1× and 1.7×, between 1.1× and 1.6×, between 1.1× and 1.5×, etc.).

Unfortunately, when performing an in situ deployment, it has proven particularly difficult to provide a tractor having an open end region into which the distal end of the catheter may be easily, reliably and robustly inserted between the expanded tractor and the inner puller/puller, particularly when the apparatus is deployed within a curved, bent, or tortious portion of the body. If the catheter distal end does not clearly and cleanly enter between the outer end of the tractor and the puller/pusher, it may get caught on the tractor and may prevent successful operation.

Described herein are methods and apparatuses for improving and enhancing deployment, and particularly in situ deployment, of the apparatus so that the distal end (tip) of the catheter can be deployed distally between the free tractor end and a puller/pusher to which the other end of the tractor is attached and inverted.

For example, described herein are mechanical thrombectomy apparatus for removing a clot from a vessel. Any of these methods an apparatuses may include an annular bias that holds the flexible tractor tube open so that an elongate inversion support catheter can be inserted through the annular bias and between the flexible tractor tube and the elongate puller/pusher ("elongate puller") to prepare the apparatus for rolling the flexible tractor tube over the distal end opening of the elongate inversion support catheter, even where the flexible tractor tube is expanding from a collapsed configuration within the elongate inversion support catheter.

For example, an apparatus as described herein may include: an elongate inversion support catheter having a distal end and a distal end opening; an elongate puller extending within the elongate inversion support catheter; a flexible tractor tube having a free first end and a second end that is attached to a distal end region of the elongate puller, wherein the flexible tractor tube is inverted over the elongate puller and is held within the elongate inversion support catheter in a collapsed first configuration; and an annular bias around the free first end of the flexible tractor tube, wherein the flexible tractor tube is configured to be extended from the distal end opening of the elongate inversion support catheter and to expand into an expanded second configuration, wherein the annular bias has a diameter that is larger than an outer diameter of the elongate inversion support catheter in the expanded second configuration (e.g., between 1.1 and 10 times the OD of the elongate inversion support catheter in the expanded second configuration, between 1.1× and 10×, etc.).

For example, a mechanical thrombectomy apparatus for removing a clot from a vessel may include: an elongate inversion support catheter having a distal end and a distal end opening; an elongate puller extending within the elongate inversion support catheter, wherein the elongate puller comprises a central lumen; a flexible tractor tube having a free first end and a second end that is attached to a distal end region of the elongate puller, wherein the flexible tractor tube comprises a woven, braided, mesh or knitted material and is inverted over the elongate puller and is held within the elongate inversion support catheter in a collapsed first configuration; further wherein the flexible tractor tube is biased to expand to between 1.1 and 4 times an outer diameter of the elongate inversion support catheter in an un-inverted configuration and is further biased to expand to greater than 0.5× an inner diameter of the elongate inversion support catheter in an inverted configuration; and an annular bias around the free first end of the flexible tractor tube, wherein the flexible tractor tube is configured to be extended from the distal end opening of the elongate inversion support catheter and to expand into an expanded second configuration, wherein the annular bias has a diameter that is larger than (e.g., greater than 1.1 times, etc.) the outer diameter of the elongate inversion support catheter in the expanded second configuration so that the elongate inversion support catheter may be pushed through the annular bias and between the flexible tractor tube and an outer diameter of the elongate puller.

The annular bias may be any appropriate bias, including a ring, a stent (e.g., a stent having a zig-zag strut pattern), a lobed bias, etc. The annular bias may be attached the free, open end of the flexible tractor tube. The annual bias may be attached by stitching, adhesive, etc. Alternatively or additionally, the annular bias may be formed by shape-setting the open end of the flexible tractor tube.

In particular, the flexible tractor tube may be biased to expand to between 1.1 and 4 times the outer diameter of the elongate inversion support catheter in an un-inverted configuration and may further be biased to expand to greater than 0.5× an inner diameter of the elongate inversion support catheter in an inverted configuration.

The elongate inversion support catheter may be configured to be pushed through the annular bias and between the flexible tractor tube and an outer diameter of the elongate puller when the flexible tractor tube is in the expanded second configuration.

In general, the flexible tractor tube may comprise a woven, braided, mesh or knitted material. For example, the flexible tractor tube may be a knitted material. The flexible tractor tube is typically formed of a soft material that may readily roll over the distal open end of the elongate inversion support catheter. For example, the flexible tractor tube may be sufficiently soft such that without support, it collapses radially under an axial compression of less than 200 g of force. The flexible tractor tube may comprise steel, polyester, nylon, expanded Polytetrafluoroethylene (ePTFE), Nitinol, or a fabric.

Any of these apparatuses may be configured for use with a guidewire. For example, any of these apparatuses may be configured to include a guidewire lumen extending through the elongate puller that is configured to pass a guidewire.

Although any appropriate elongate inversion support catheter may be used, in particular, the elongate inversion support catheter may have a harness profile such that this distal end is generally soft, until the very distal end, which may be harder than the more proximal region (e.g., the distal most 5 mm, distal most 4 mm, distal most 3 mm, distal-most 2 mm, distal most 1 mm, etc. has a hardness that is greater than the region immediately proximal, which otherwise gradually becomes softer along the distal length). For example, the material hardness of the elongate inversion support catheter may generally decrease over the distal end of the catheter until the distal end opening, wherein the distal end opening may have a material hardness that is greater than a material hardness of a region immediately proximal to the distal end, further wherein the distal end opening has a rounded lip profile.

The elongate puller may comprise a hypotube.

The flexible tractor tube may be any appropriate length. For example, the flexible tractor tube may be between 3 cm to 50 cm long.

Also described herein are methods of deploying a mechanical thrombectomy apparatus for removing a clot from a vessel. For example, any of these methods may include: positioning an elongate inversion support catheter within a lumen of the vessel; extending an elongate puller and a flexible tractor tube out of a distal of the elongate inversion support catheter, wherein the flexible tractor tube has a free first end coupled to an annular bias and a second end that is attached to a distal end region of the elongate puller so that the flexible tractor tube expands from a collapsed first configuration within the elongate inversion support catheter into an expanded second configuration, wherein the annular bias in the expanded second configuration holds the flexible tractor tube open to a diameter that is between 1.1 and 5 times an outer diameter of the elongate inversion support catheter; advancing the elongate inversion support catheter distally through the annular bias and between the flexible tractor tube and the elongate puller; and pulling the elongate puller proximally to roll the flexible tractor tube over a distal end opening of the elongate inversion support catheter so that it inverts into the elongate inversion support catheter, wherein the flexible tractor tube is biased to expand to between 1.1 and 4 times an outer diameter of the elongate inversion support catheter in an un-inverted configuration and is further biased to expand to greater than 0.5× an inner diameter of the elongate inversion support catheter in an inverted configuration within the elongate inversion support catheter.

Any of these methods may also include grabbing a clot from within the vessel and into the elongate inversion support catheter by rolling the flexible tractor tube over the distal end opening.

Positioning an elongate inversion support catheter within the lumen of the vessel may include extending the elongate inversion support catheter over a guidewire. Extending the elongate puller and the flexible tractor tube out of the distal of the elongate inversion support catheter may include pushing the elongate puller distally out of the elongate inversion support catheter. Extending the elongate puller and the flexible tractor tube out of the distal of the elongate inversion support catheter may comprise expanding the annular bias, further wherein the annular bias comprises a stent coupled to the free first end of the flexible tractor tube.

Extending the elongate puller and the flexible tractor tube out of the distal end opening of the elongate inversion support catheter may comprise extending a woven, braided, mesh or knitted material forming the flexible tractor tube out of the distal end opening of the elongate inversion support catheter.

Any of these methods may include supporting the flexible tractor tube over the distal end opening so that the flexible tractor rube does not radially collapse under axial compression, wherein the flexible tractor tube is sufficiently soft such that without support, it collapses radially under an axial compression of less than 200 g of force.

The elongate inversion support catheter of the any of the apparatuses described herein may be or may include (particularly at its distal end) any appropriate catheter, e.g., a flexible tube that can be inserted into a body vessel (e.g., blood vessel) into which the more flexible tractor portion can be withdrawn by pulling against the elongate inversion support. The elongate inversion support catheter may, in some variations, also be referred to as an outer catheter (e.g., when the puller for the tractor is referred to as an inner catheter) and/or inversion catheters and/or support catheter, as it may support the inversion of the tractor around the distal end opening of the catheter. The elongate inversion support catheter may include a braided or woven portion, a spiral or coiled portion, etc. (e.g., having a braided shaft), may have a single layer or multiple layers, and may be formed of biocompatible materials, including polymers, metals, etc. (e.g., PTFE). Examples of vascular catheters that may form the elongate inversion support include micro catheters.

The flexible tractor tube may be referred to as simply a tractor or as a tractor region, and may be configured to prevent jamming, while still able to efficiently "grab" a clot from within a vessel. For example, described herein are mechanical thrombectomy apparatuses that may be configured to grab or grasp a clot as it is mechanically drawn into the apparatus for removal. Although suction may be used in addition to the mechanical grabbing of the clot, in some variations suction is not used.

The flexible tractor tube may include projections that extend from the tractor region, particularly or exclusively as it bends around during inverting (e.g., at the distal end of the device). These projections may remain flat or non-extending when the tractor is held in parallel with the elongate inversion support. Alternatively, the projections may extend at all times. In general, the tractor may be formed of a woven materials, knitted material, or laser-cut sheet of material. The knitted and/or woven materials may be fibrous materials (including natural fibers, synthetics fibers, etc.), polymeric materials, or the like. For example, the material (e.g., strands) forming the woven or knitted material may be one or more of: monofilament polymer, multifilament polymer, NiTi filament, NiTi tube with radiopaque metallic center, Cobalt chromium alloy filament, Cobalt chromium alloy tube with radiopaque metallic center, Nylon, Polyester, Polyethylene terephthalate, and Polypropylene. The sheets of material (e.g. a solid sheet of material) formed into the tractor region may be one or more of: polymeric material (e.g., PTFE), silicone materials, polyurethanes, shape memory alloys, stainless steels, etc. The sheets may be extruded, glued, or the like. The sheets may be cut to form pores and/or projections. For example, the sheets may include one or more laser-cut projections. Any of these apparatuses may be coated with a hydrophilic and/or hydrophobic coating, and/or may include pores. The tractor may have a porosity of greater than >60% (greater than 70%, greater than 75%, greater than 80%, greater than 85%, etc., between 60-95, 65-95, 70-95%, etc.).

In any of the apparatuses described herein, the elongate inversion support catheter may be adapted to enhance rolling of the tractor region (inverting) over the distal end. For example, in any of the apparatuses described herein, the catheter may be configured so that the material hardness of the catheter decreases over the distal end of the catheter until the distal end opening, wherein the distal end opening has a material hardness that is greater than a material hardness of a region immediately proximal to the distal end, further wherein the distal end opening has a rounded lip profile. The catheter distal end may be stiffer because it is thicker (e.g., it may be formed by inverting the distal end of the catheter back over itself, and/or it may be formed of a stiffer material than the adjacent more proximal region (including by including a reinforcing material).

In any of the apparatuses described herein, the flexible tractor tube may include one or more coatings from the group of: a lubricious coating, a metal coating, a heparin coating, an adhesive coating, and a drug coating. In particular the tractor may include a uniform or non-uniform lubricious (e.g., hydrophilic) coating.

As mentioned, any of these apparatuses may include a puller, e.g., an elongate puller coupled to a distal end of the tractor. Any of these apparatuses may include an elongate puller within the catheter coupled to a distal end of the tractor. The elongate puller may comprise a hypotube having an inner lumen that is continuous with the guidewire lumen though the flexible tube.

In general, the tractor may be any appropriate length. For example, the tractor may be between 3 to 100 cm long (e.g., between 3 and 50 cm, between 3 and 40 cm, between 3 and 30 cm, between 3 and 20 cm, between 10 and 100 cm, between 10 and 50 cm, between 20 and 100 cm, between 20 and 50 cm, etc.).

In any of these apparatuses, the apparatus may be configured so that the tractor may be inverted and rolled into the catheter by applying less than 300 grams of force (e.g., less than 400 g of force, less than 300 g of force, less than 200 g of force, less than 100 g of force, less than 90 g of force, less 80 g of force, less than 70 g of force, less than 60 g of force, less than 50 g of force, less than 10 g of force, etc.) to a distal end of the flexible tube, e.g., by pulling the elongate puller. For example, as mentioned above, the apparatus may include a hydrophilic coating, a lubricant on the catheter and/or tractor, a sleeve between the tractor and catheter, etc. This force required to retract the tractor into the catheter typically refers to the force required to roll the tractor over the distal end of the tractor.

Any of the apparatuses described herein may be configured so that the tractor is highly soft, and therefore rolls around the distal end of the catheter forming the elongate inversion support easily without jamming and/or requiring a large force to roll the tractor over the distal end opening of the catheter. In particular, tractors having a low axial compression strength, that would, but for the elongate inversion support, typically buckle, have been found to prevent jamming of the elongate inversion support as the tractor inverts. In particular, unsupported tractors (e.g., tractor that are not rolling over a catheter supported annular opening) that are configured to collapse radially under an axial compression of less than about 500 g of force (e.g., less than: about 500 g force, about 400 g force, about 300 g force, about 200 g force, about 150 g force, about 100 g force, about 50 g force, etc.) may be particularly helpful in preventing jamming. For most knitted, woven, and braided tractors, including those described herein, when the tractor is configured to withstand greater that this amount of axial compression force, the tractor may jam, and/or may require excessive force to invert. Thus, in any of the apparatuses and methods described herein, the tractor maybe sufficiently soft such that without support from the catheter, the tractor collapses radially under an axial compression of less than 200 g of force when inverting (and may instead buckle).

Further, in any of the apparatuses described herein, the tractor may be biased to expand to greater than the outer diameter of the catheter in a second configuration (that is inverted relative to the first configuration) where the tractor is extending over the outer diameter of the catheter. The same tractor may be biased to expand to greater than the inner diameter of the catheter of the elongate inversion support in the first (e.g., un-inverted) configuration where the tractor is within the catheter of the elongate inversion support. Thus, in relaxed configuration, prior to assembling with the elongate inversion support, the tractor may be oversized compared to the catheter of the elongate inversion support; the portion of the tractor that extends within the catheter of the elongate inversion support, referred to as "un-inverted," may have an inner diameter that is greater than the inner diameter of the catheter, which may tend to drive the tractor toward the walls of the inner diameter of the catheter without collapsing down into the catheter. Further, the inner diameter of the tractor in the "inverted" configuration, e.g., the configuration of the portion that is doubled back over and along the catheter of the elongate inversion support, may be greater than the outer diameter of the catheter of the elongate inversion support. This arrangement may prevent jamming and an increased resistance between the tractor and the outside of the catheter of the elongate inversion support. The catheter may be biased to expand in both the inverted and un-inverted configurations by, e.g., heat setting. The tractor may be inverted to transition between the first and second configurations by rolling over the distal end of the catheter; the terms "inverted" and "un-inverted" are therefore relative terms.

The annular bias may be biased to have an expanded, open configuration that has a slightly larger (e.g., greater than 5%, greater than 10%, greater than 15%, greater than 20%, greater than 25%, etc., larger than the expanded diameter of the flexible tractor tube. In addition, the annular bias may be relatively "stiffer" than the open (free) end of the flexible tractor tube, to prevent buckling, collapse, etc. In some variations, the annular bias has a smooth and/or curved edge to prevent getting caught on the elongate inversion support catheter when it is inserted into the annular bias.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1I illustrate examples of apparatuses for mechanically removing an object such as a clot form a body region. FIG. 1A shows an example of an elongate inversion support catheter portion of an apparatus. At least the distal end of the elongate inversion support is configured as a catheter. FIG. 1B shows an enlarged view of a partial section of a distal end (opening) of the catheter of the elongate inversion support of FIG. 1A, showing the aperture formed by the distal end opening; FIG. 1C shows an example of a flexible tractor tube attached over a puller (the puller in this example is configured as a catheter). The tractor is shown in a first configuration. In some variations, the flexible tractor tube may be biased open, e.g., by heat setting, to have an outer diameter that is greater than the inner diameter of the catheter of the elongate inversion support, as shown in FIG. 1D. FIG. 1D shows the same distal tractor region of FIG. 1C with the expandable first end region expanded. This first configuration may be compressed down into the elongate inversion support and the distal end inverted over the catheter portion of the elongate inversion support, as shown in FIG. 1E. In FIG. 1E, the assembled mechanical thrombectomy apparatus includes an elongate inversion support catheter having a distal end and a distal end opening; the elongate puller extends within the elongate inversion support catheter and a flexible tractor tube is connected at one end to the elongate puller. The flexible tractor tube and puller may be extended through the elongate inversion support catheter, including extended out of the distal end (e.g., by pulling the elongate inversion support catheter proximally and/or by pushing the elongate puller distally). The flexible tractor tube may initially be held in a collapsed first configuration (as shown in FIG. 1E) for positioning within a vessel; it may be deployed and expanded, as shown in FIG. 1F, with the elongate inversion support catheter positioned between the flexible tractor tube and the elongate puller. The flexible tractor tube may be biased so that in the second configuration (inverted over the distal end of the catheter), the tractor has a 'relaxed' outer diameter that is greater than the outer diameter of the catheter of the elongate inversion support.

FIGS. 1G and 1H illustrate the use of the an apparatus such as the one shown in FIGS. 1E and 1F to remove a clot by drawing the flexible tractor tube proximally and/or advancing the catheter distally towards the clot so that the expandable first end region inverts as it is drawn into the distal end of the catheter, pulling the clot into the catheter.

FIG. 1I illustrates an alternative variation of a tractor and puller. In FIG. 1I, the tractor is shown attached to the distal end of a tapered or narrow puller; the distal end region is tapered, and includes a radiopaque marker at or near the attachment site to the tractor; the tractor may be knitted, braided, woven, etc. Thus, in some variations the distal end region of the puller may have a greater flexibility than the proximal end of the puller. The puller may be hollow (e.g., a catheter or hypotube) or solid (e.g., like a wire).

FIGS. 2A-2F illustrate one (in situ) method of deploying a mechanical thrombectomy apparatus. In FIG. 2A the elongate inversion support catheter (either alone or with a guidewire) is positioned within the vessel, near a clot. In some variations the flexible tractor tube and elongate puller may already be positioned within the elongate inversion support catheter, e.g., near the distal end, or it may be moved into position thereafter, as shown in FIG. 2B. In FIG. 2C, the flexible tractor tube is deployed out of the elongate inversion support catheter and allowed to expand. Thereafter, the elongate inversion support catheter is moved distally between the flexible tractor tube and the elongate puller, as shown in FIG. 2D. Once the elongate inversion support catheter is positioned distally between the flexible tractor tube and elongate puller, as shown in FIG. 2E, the flexible tractor tube may be rolled and inverted into the elongate inversion support catheter, as shown in FIG. 2F. In this example, the inverting flexible tractor tube is shown grabbing a clot may as it is inverted into the elongate inversion support catheter. The flexible tractor tube extends from the distal end opening of the elongate inversion support catheter and expands into an expanded second configuration; the flexible tractor tube is biased to expand to between 1.1 and 4 times an outer diameter of the elongate inversion support catheter in an un-inverted configuration (e.g., FIG. 2D) and is further biased to expand to greater than 0.5× an inner diameter of the elongate inversion support catheter in an inverted configuration (when drawn into the catheter as shown in FIG. 2F).

FIGS. 3A-3B illustrate a first variation of an apparatus having an elongate puller with a stepped outer diameter into which the flexible tractor tube may be compressed. This configuration may provide improved mobility within the elongate inversion support catheter. This variation may also be readily adapted for application to a vacuum through the hollow elongate puller. In FIG. 3A the flexible tractor tube is collapsed. In FIG. 3B the flexible tractor tube is expanded, as shown.

In FIG. 4A the elongate puller is positioned at the distal end of the elongate inversion support catheter, and extended from the distal end opening of the catheter until the collapsed flexible tractor tube is expanded at least slightly, as shown in FIG. 4B. An annular bias, described in greater detail below, may be used in this variation as well. As shown in FIG. 4C, the elongate inversion support catheter may then be positioned between the flexible tractor tube and the elongate puller, so that the elongate inversion support catheter can support the flexible tractor tube until it can be pulled proximally by pulling the elongate puller to invert into the elongate inversion support catheter.

In FIG. 5A the elongate inversion support catheter is positioned near the clot in the vessel. The elongate pusher to which a flexible tractor tube is attached at a first end, with an annular bias on an open, free second end, is extended distally through the catheter and out of the distal end of the elongate inversion support catheter, as shown in FIG. 5B. In FIG. 5C, the annular bias holds the free end of the flexible tractor tube open. In some variations the flexible tractor tube is biased to expand to diameter that is slightly greater than the outer diameter of the catheter (e.g., greater than 1.1× the outer diameter of the elongate inversion support catheter), however the annular bias may be open even slightly more, and may be more rigid when expanded open, as shown. The elongate inversion support catheter may then be inserted distally through the annular bias and between the flexible tractor tube and the elongate puller, as shown in FIGS. 5D-5E. A vacuum may be applied through the elongate puller and/or elongate inversion support catheter, as shown in FIG. 5E. In FIG. 5F, withdrawing the elongate puller proximally (with or without a vacuum) to roll the flexible tractor over the distal end of the elongate inversion support catheter so that it inverts into the elongate inversion support catheter may draw the clot into the elongate inversion support catheter, as shown.

FIGS. 6A-6F illustrate another variation of an apparatus including an annular bias on an open, free, end of the flexible tractor tube. In FIG. 6A, the elongate inversion support catheter is positioned, shown here with the optional use of a guidewire, within the lumen of the vessel. In FIG. 6B, the elongate puller and flexible tractor tube are positioned distally within the elongate inversion support catheter, also over the guidewire; the flexible tractor tube is attached at one end of the flexible tractor tube, with the other end of the flexible tractor tube attached to an annular bias at a free (loose) end. The guidewire may be removed or left in position when deploying the flexible tractor tube from the distal end of the elongate inversion support catheter. In FIG. 6C, the distal end of the puller including the entire flexible tractor tube is extended distally from the elongate inversion support catheter and the annular bias expands to a diameter that is greater than the outer diameter of the elongate inversion support catheter. In FIGS. 6D and 6E, the elongate inversion support catheter is advanced distally within the annular bias and between the flexible tractor tube and the elongate puller, so that the elongate inversion support catheter may support the flexible tractor tube as it is pulled proximally by the elongate puller to invert over the distal end opening of the elongate inversion support catheter. The apparatus may be advanced (e.g., while pulling the elongate puller proximally) to grab and remove a clot from the vessel, as shown in FIG. 6E.

In FIG. 7A, a ring-shaped annular bias is shown. In FIG. 7B the annular bias is a member having lobes or petals, which may predictably collapse when compressed (e.g., see the collapsed end view). In FIG. 7C the annular bias is a stent-like structure having a plurality of zig-zagging struts (members).

FIGS. 8A-8C illustrate an example of an apparatus including a flexible tractor tube having a stent-like annular bias (formed of a loop of a sinusoidally arranged strut(s) having a 0.002" thickness attached to the open end of a 144 end 0.00075" NiTi braid flexible tractor tube). FIG. 8A sows the expanded annular bias, shown attached to the flexible tractor tube in FIG. 8B. The flexible tractor tube with the annular bias of FIG. 8A is shown attached to an elongate puller in FIG. 8C.

FIG. 9A shows another example of a flexible tractor tube (144 end 0.00075" NiTi) having an annular bias. FIG. 9B shows the open end of the flexile tractor tube rolling over the open distal end of the elongate inversion support catheter. FIG. 9C shows a schematic of the stent-like annular bias including lead-in arms that may help it roll over the elongate inversion support catheter.

In FIG. 10, the open (loose) end of the flexible tractor tube folds back under itself which may help guide the elongate inversion support catheter into the space between the flexible tractor tube and the elongate puller. In this example, the flexible tractor tube may not require an additional annular bias.

DETAILED DESCRIPTION

In general, described herein are mechanical thrombectomy apparatuses having an inverting flexible tractor tube that is configured to be deployed in situ (e.g., within a catheter) without jamming. Any of these apparatuses may include an elongate elongate inversion support catheter over which the flexible tractor tube inverts at the distal end. In the deployment configuration, the flexible tractor tube may comprise a flexible tube that doubles back (e.g., inverts) over the distal end opening of the elongate inverting support catheter so that the tractor tube extends into the opening of the elongate inverting support catheter when the tractor tube is pulled proximally. The tractor tube may be attached at one end to an elongate puller. Pulling the elongate puller proximally will roll and invert the tractor over the distal end opening of the elongate inverting support catheter which may capture a clot and pull it into the elongate inversion support catheter.

Any of the apparatuses may include a coating (e.g., hydrophilic, lubricious coating, etc.) or the like to enhance the sliding and inverting of the tractor over the distal end. Further, any of these apparatuses may include one or more projections that are configured to enhance grabbing and/or maceration of a clot.

In general, a mechanical thrombectomy apparatus for removing a clot from a vessel may be a system, assembly or device including an elongate inversion support catheter having a distal end and a distal annulus (distal end opening), and a flexible tractor assembly including a flexible tractor tube coupled to an elongate puller. The flexible tractor tube is configured to roll and invert over the distal end opening of the elongate inverting support catheter.

In many of the examples described herein, the tractor assembly is configured to extend within the elongate inversion support catheter when deployed. Any of these apparatuses may switch between a delivery configuration, e.g., in which the entire tractor assembly may be held within the elongate inversion support catheter prior to deployment, and a deployed configuration, e.g., in which the elongate inversion support catheter is positioned between the flexible tractor tube and the elongate pusher to support the flexible tractor tube as it is pulled into the elongate inversion support catheter distal end opening to roll and invert into the elongate inversion support catheter. In particular, the methods and apparatuses may be configured so that the transition between the delivery configuration and the deployed configuration is robust. For example, as will be described in greater detail herein, any of the apparatuses and methods described herein may include an annular bias that enhances the ability of the elongate inversion support catheter to be inserted between the flexible tractor tube and the elongate puller.

Figure 1E:
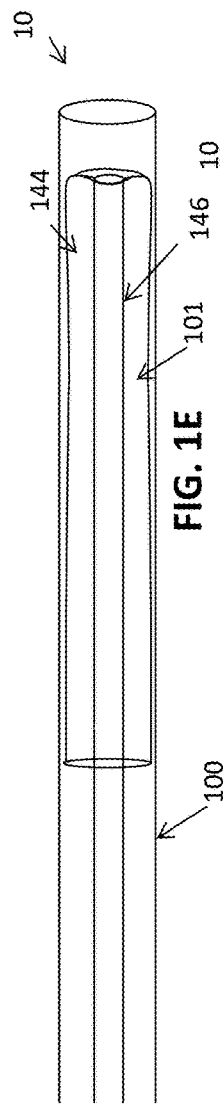

FIGS. 1A to 1I illustrate various components of a mechanical thrombectomy apparatus that may include any of the features described herein. For example, FIG. 1A shows a catheter (e.g., an elongate inversion support catheter) that may form part of the apparatuses described herein. In this example, the elongate inversion support catheter includes a catheter body 100 having a distal end region 103 that includes a distal end opening 105. The distal end region may have an increasing softness (measured by durometer, e.g., shore durometer) except that the very distal-most end region (distal end 105, including the distal end opening) may be substantially less soft than the region immediately proximate to it. Thus, although the distal tip region of the catheter (e.g., the distal most x linear dimensions, where x is 10 cm, 7 cm, 5 cm, 4 cm, 3 cm, 2 cm, 1 cm, 9 mm, 8 mm, 7 mm, 6 mm, 5 mm, 4 mm, 3 mm) has an increasing softness/decreasing harness extending from the proximal to distal ends, the very distal end region 107 (e.g., measured as distal most z linear dimensions, where z is 1 cm, 9 mm, 8 mm, 7 mm, 6 mm, 5 mm, 4 mm, 3 mm, 2 mm, 1 mm, 0.8 mm, 0.5 mm, 0.3 mm, 0.2 mm, etc., and z is always at least three times less than x) has a hardness that is greater than the hardness of the region immediately proximal to it, and may be as hard or harder than the proximal-most region of the distal tip region.

In FIG. 1A, the elongate inversion support catheter is an elongate hollow catheter having a column strength that is sufficient to prevent buckling when the catheter is pulled over the distal annulus (distal end opening). Thus, the elongate inversion support may be configured so that it does not collapse (e.g., buckle) when 500 g or less of of compressive force is applied (e.g., at least about 700 g, 600 g, 500 g, 400 g, 300 g, etc. of compressive force) for neurovascular applications. For peripheral vascular applications the elongate inversion support may be selected or configured to withstand at least 1500 g of compressive force (e.g., at least about 2000 g, 1900 g, 1800 g, 1700 g, 1600 g, 1500 g, 1400 g, etc. of compressive force). In general, any of the apparatuses described herein may include an elongate inversion support catheter that is not a full-length catheter, but may include a portion of a catheter, typically at the distal end, connected to a rod, wire, hypotube, or the like. In FIG. 1A the catheter 100 of the elongate inversion support catheter may be any appropriate type of catheter or portion of a catheter, including microcatheters appropriate for neurovascular use.

In some variations the distal end 105 of the elongate inversion support is adapted so that the tractor may slide or roll and invert over the distal end of the catheter without being caught (binding, jamming) or without substantial friction. For example, in some variations the distal tip (end) may be curved or radiused 109 as shown in FIG. 1B, particularly on the outer surface (e.g., the transition from outer diameter to inner diameter).

FIG. 1C shows an example of a flexible tractor tube 144 coupled to an elongate puller 146, forming a pullable tractor assembly 140. In this example, the tractor tube is shown integrated with the puller and extending back over the puller, forming the assembly. The opposite end of the flexible tractor tube 147 is open and free (e.g., not connected to the puller or catheter). As will be described in greater detail below, this open, free, end may be adapted to be expanded and held open, e.g., by shape setting back on itself and/or by including an annular bias, to enhance deployment and positioning of the catheter between the flexible tractor tube and the puller. In FIG. 1C, the tractor tube is formed of material (e.g., wove, knitted, braided, etc.) that is flexible and elongate. The tractor is shown extended from the puller in a first configuration. It may be particularly beneficial if the relaxed outer diameter of the flexible tractor in this first configuration has a greater outer diameter than the outer diameter of the catheter of the elongate inversion support into which the tractor will be positioned prior to inverting. The flexible and tubular tractor 144 may be sufficiently soft and flexible (e.g., having a low collapse strength) so as to easily roll and fold over the distal aperture of the elongate inversion support. The puller 146 may typically be a less-expandable (or non-expandable) structure (tube, puller, etc.). For example, the tractor 144 may be configured, e.g., by shape-setting (heat setting, etc.), to expand in the relaxed first configuration to a radial diameter that is between 1.1 and 10 times (e.g., between 1.1× and 5×, between 1.1× and 4×, etc.) the diameter of the inner diameter of the catheter of the elongate inversion support when unconstrained. In FIG. 1D, the tractor tube has a larger expanded diameter than the variation shown in FIG. 1C in a relaxed configuration. In any of these variations, the expandable tractor may be biased to expand open. The tractor may be formed of a mesh, braided, woven, knitted, or sheet of material and is generally adapted to grasp the object to be removed (e.g., blood clot).

In FIGS. 1C and 1D the tractor and puller have two portions, a tractor tube 144 and a less expandable (or non-expandable) proximal portion comprising the elongate puller 146. The puller may be a separate region, such as a wire, catheter or hypotube, which is connected to an end region of the tractor (e.g., a flexible mesh, woven, braided, etc.), e.g., the distal end or near the distal end. The inverting region of the tractor, where it rolls and inverts over the distal end opening of the catheter may be referred to as the distal-facing region of the tractor, which may actively grab clot when rolling.

In FIG. 1E, the tractor assembly (flexible tractor tube 144 and puller 146 of FIG. 1D) are shown within an elongate inversion support catheter 100. The tractor is collapsed down 101, e.g., onto the puller, and may be held collapsed within the elongate inversion support catheter. Thus, FIG. 1E shows the pre-deployment (e.g., delivery) configuration. The tractor assembly may be axially movable (slidable) within the catheter so that it can be positioned within the catheter and within the vessel.

Figure 1F:
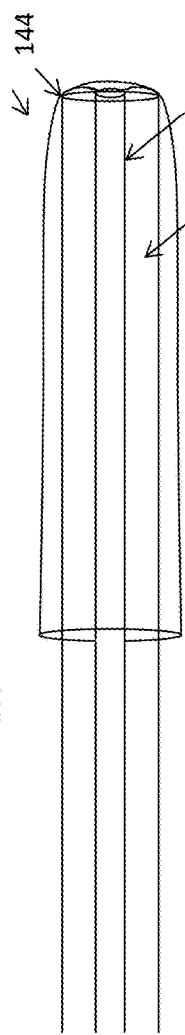

FIG. 1F shows a fully deployed apparatus. In FIG. 1F, the tractor tube is in an unconstrained or deployed configuration, and the elongate inversion support catheter is positioned between the tractor tube and the puller so that the tractor tube can be pulled proximally by pulling on the puller and rolling the tractor tube into the elongate inversion support catheter so that it inverts. In FIG. 1F, the tractor in this deployed configuration (e.g., the portion that is inverted over the distal end of the catheter) has an outer diameter that is greater than the outer diameter of the catheter of the elongate inversion support. Thus, the tractor 144 may be biased so that it has a relaxed expanded configuration with a diameter that is greater than the outer diameter (OD) of the elongate inversion support catheter; in addition, as will be described in relation to FIGS. 1G and 1H, below, the tractor tube may also be configured (e.g., by heat setting, etc.) so that when the tractor tube is inverted and pulled into the elongate inversion support catheter, the outer diameter of the inverted tractor tube has an outer diameter that is greater than 0.5× (e.g., greater than 0.6×, greater than 0.7×, greater than 0.75×, greater than 0.8×, greater than 0.9×, greater than 1×, etc.) the inner diameter (ID) of the elongate inversion support catheter. This combination of an un-inverted diameter of the tractor tube of greater than the diameter of the OD of the elongate inversion support catheter and an inverted diameter of the tractor tube of greater than 0.7× the ID of the elongate inversion support catheter is surprisingly helpful for preventing jamming of the apparatus, both when deploying the apparatus and when rolling the tractor over the distal end opening of the elongate inversion support catheter to grab a clot. The tractor may be expandable and may be coupled to the puller as shown. In some variations the flexible tractor and the puller may comprise the same material but the tractor may be more flexible and/or expandable, or may be connected to elongate puller (e.g., a push/pull wire or catheter).

Figure 1G:
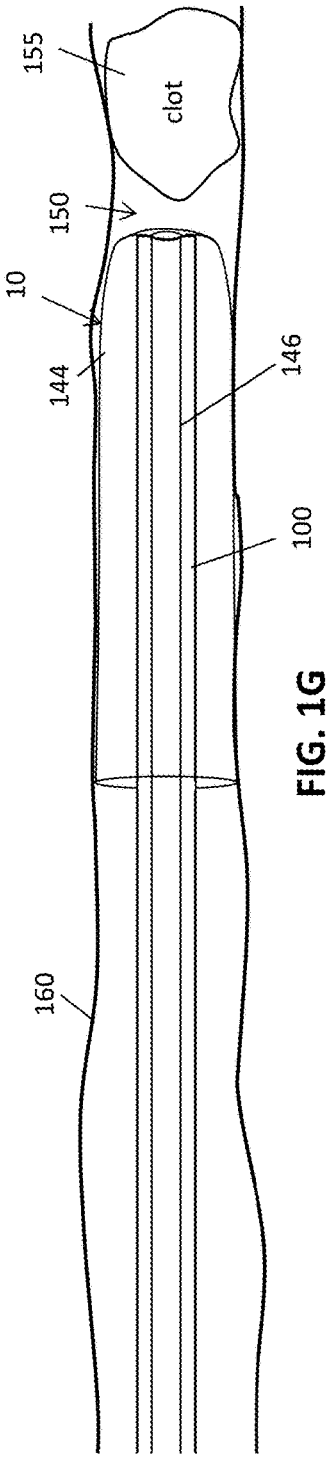
Figure 1H:
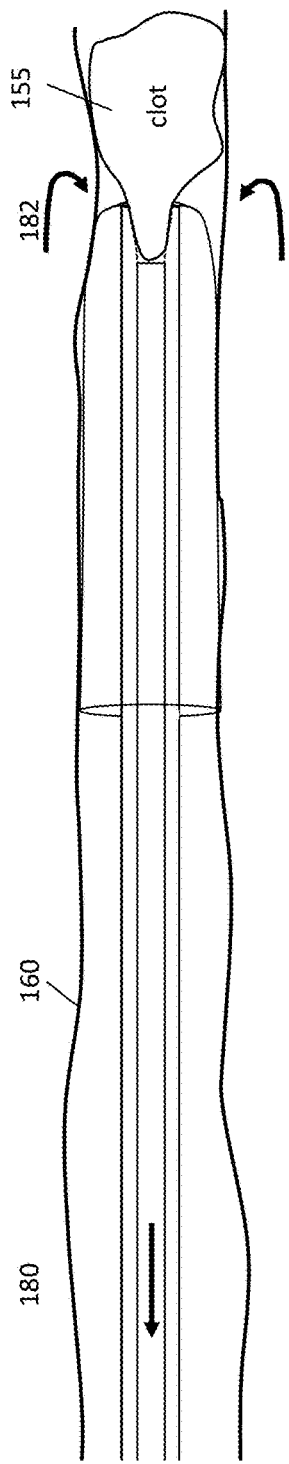
Figure 1I:
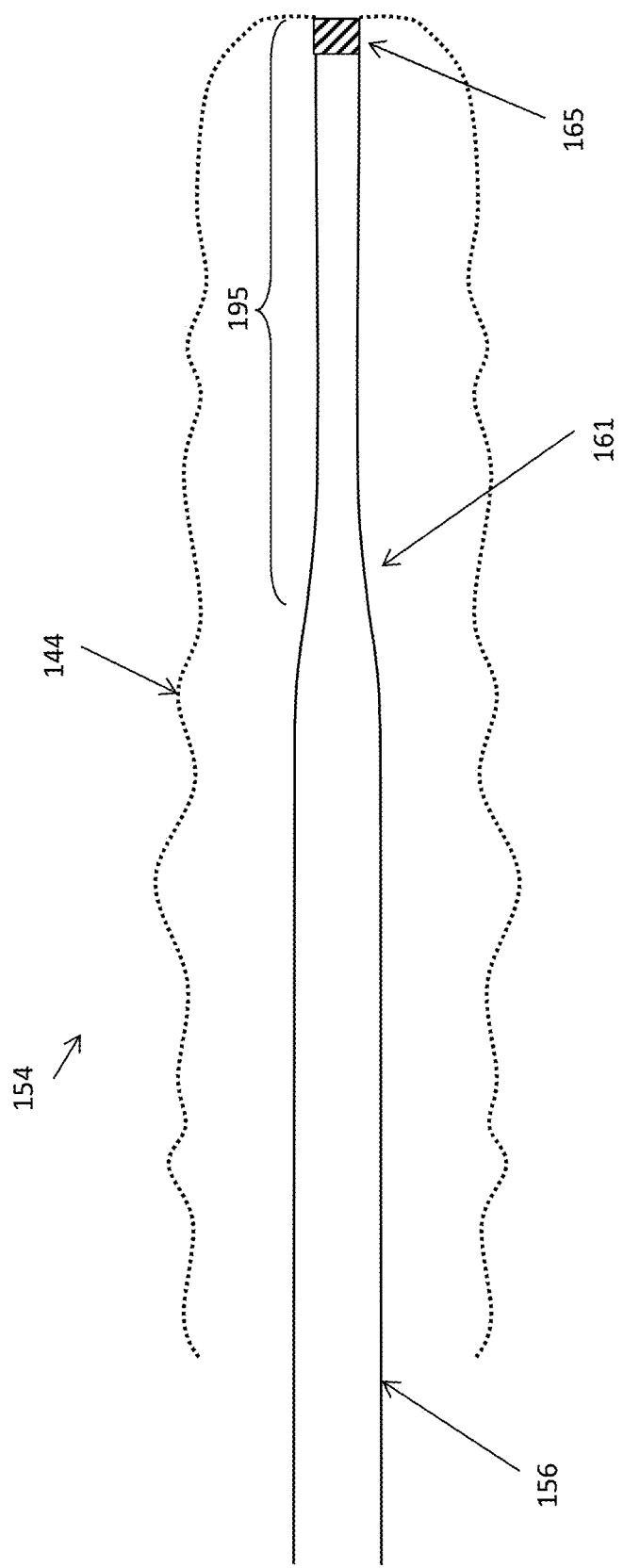

FIGS. 1G and 1H illustrate the removal of a clot using an apparatus such as the apparatus components of FIGS. 1A and 1E. The apparatus 10 is shown in a deployed state. In this example the thrombectomy apparatus 10 is configured as a thrombectomy apparatus including an elongate inversion support catheter 100 and a flexible tractor tube 144 that extends over the distal end region of the catheter and doubles-over itself at the distal end of the catheter to invert so that the external tractor end region is continuous with an inner, less-expandable (in this example, less-expandable includes non-expandable) second distal end region 146 (puller) that extends proximally within the catheter and forms an inner lumen that may pass a guidewire. The pusher/puller member that may be a rod or other member that is continuous with the distal end region of the tractor. In FIG. 1G the apparatus is shown positioned and deployed within the vessel 160 near a clot 155. The clot may be drawn into the catheter by pulling the tractor 140 proximally into the catheter 101, as indicated by the arrow 180 showing pulling of the inner portion of the flexible tractor (e.g., using a handle, not shown) resulting in rolling the tractor over the end opening of the catheter and into the catheter distal end and inverting the expandable distal end region so that it is pulled into the catheter, shown by arrows 182. The end of the tractor outside of the catheter may be "loose" relative to the outer wall of the catheter. FIG. 1I illustrates another example of a tractor assembly 154 including a tractor tube 144 that is coupled to a puller 156. The puller in this example is tapered (having tapering region 161) and may therefore have a different flexibility of the distal end region than the proximal end region. For example the proximal end region may be less flexible than the narrower-diameter distal end region 195 to which the tractor is coupled. The assembly includes a radiopaque marker 165. The tractor may be attached to the puller by any appropriate means. For example, the tractor may be crimped, glued, fused, or otherwise attached to the puller, typically permanently.

In general the mechanical thrombectomy apparatuses described herein may be highly flexible, both before actuating and during operation. For example, the flexible tractor may not increase the stiffness/flexibility of the catheter of the elongate inversion support, and particularly the distal end region of the catheter too much, to avoid impacting maneuverability, particularly within tortious vessels of the neurovasculature. Described herein are flexible tractor tube portions that increase the stiffness of the last y cm (e.g., distal most 20 cm, 18 cm, 15 cm, 12 cm, 10 cm, 9 cm, 8 cm, 7 cm, 6 cm, 5 cm, 4 cm, 3 cm, 2 cm, 1 cm, etc.) of the catheter less than a predetermined percentage (e.g., less than 10%, 12%, 15%, 18%, 20%, 25%, 30%, etc.). For example, described herein are flexible tractor tube portions that pass through the catheter and double back over the distal end of the catheter but increase the stiffness of a distal 5 cm of the catheter by less than 15% of the stiffness of the distal 5 cm of the catheter without the flexible tube extending therethrough and doubling back over the distal end of the catheter.

The tractors may be woven, braided and/or knitted materials. For woven and braided materials, which may include a plurality of fibers that are woven or braided to form the inverting tube, these structures may be tuned to prevent jamming and/or to reduce the force necessary to pull the tractor and invert over the catheter tip. For example, the mechanical atherectomy apparatus may include a braid-type tractor that can roll freely around the tip of catheter even in a tortuous anatomy and when grabbing clot by tuning one or more of the braid structure; minimizing the braid angle; including a hydrophilic coating on the distal aspect of the catheter outer diameter (OD) or the inner diameter (ID) of the braid (e.g., tractor); including a radiused wall on the catheter; and/or increasing the stiffness of the distal tip region relative to adjacent proximal regions.

As mentioned, the tractor (e.g., braided, woven, knitted, etc.) may be configured to collapse down into the inner diameter (ID) of the catheter as little as possible. For example the tractor may collapse to an ID that is greater than, equal to, or within 90%, 85%, 75%, 70%, 65%, 60%, or 50% of the catheter inner diameter (ID)/Catheter Tip OD, since, when the tractor is being pulled around catheter tip it may create axial tension on the tractor (e.g., braid, knit, etc.) that can inadvertently cause the tractor to jam on the catheter tip. When tractor is pulled around catheter tip, the tractor is being pulled in the axial orientation creating axial tension on tractor structure as the tractor is being pulled through the catheter ID. By having the tractor elements jam at an ID greater than or equal to 90%, 85%, 75%, 70%, 65%, 60%, or 50% of the catheter ID (or in some variations, OD), when being axially tensioned, the tractor is less likely to grab/synch down onto the catheter tip, helping the braid roll around the catheter tip with less axial force applied by the user. If less axial force is required by the user to pull the tractor structure around the tip then the catheter tip is less likely to buckle or deflect when retracting the tractor. It may be advantageous to minimize the chance the catheter tip will buckle. The tractor can be tuned to "jam" at a specific ID by controlling any of the following variables and in any combination: selecting a specific number of braid ends, selecting the size/diameter of the braid ends; selecting the braid material (e.g., multifilament or monofilament); heat setting the bias on the braid (e.g., braid diameter); and selecting a braid pattern, e.g., 1×2, 1×1 or any other pattern.

The braid angle may be minimized to prevent locking up of the rolling of the tractor over the catheter end opening. Typically, the lower the braid angle (e.g., 45 degrees or less, 40 degrees or less, 35 degrees or less, 30 degrees or less, 25 degrees or less, 20 degrees or less, etc.) the less likely it is to have the braid cross over points catch on the catheter tip.

In any of the variations described herein, the catheter and/or a surface of the tractor may be coated to enhance rolling over the distal end region of the catheter. It may be helpful to have a hydrophilic coating on the distal aspect of the catheter OD or the ID of the tractor so the tractor can more easily side over the catheters distal end and around the tip of the catheter when pulled through the inside of the catheter.

The radius wall of the catheter tip may be chosen/set to within a range that allows sliding. For example, it may be helpful for the tip of the catheter to have the largest radius possible but at least 0.0025" radius wall on the catheter, ideally approximately 0.005" radius wall.

The stiffness of the distal of the catheter may be sufficiently stiff to prevent collapse as the tractor is pulled; it may also be lubricious (e.g., by a coating or material property). The distal most section of the catheter tip (e.g., the last 5 mm) may be fabricated of a material which is stiff enough and lubricious enough so the distal tip of the catheter does not collapse or buckle inward ward when the braid structure is rolling around the catheter tip. Thus, the distal tip may have a stiffness that is greater than the more proximal region at the distal end of the catheter.

It may be helpful or desirable to have pores in the tractor. A lack of gaps or small pore size may limit the ability of the braid to grab clot. Alternatively or additionally, it may be desirable to form a braid structure with texture. One example is to braid two or more different diameter braid ends into the same structure: the difference in braid end diameters will help form a texture to the braid structures outer surface, aiding the grabbing of the clot when rolling the braid-dozer around the catheter tip.

As an alternative (or in addition) the tractor may be configured to lock so it does not compress in diameter during axial load by adding a coating, laminate or adhesive to the braid at a desired diameter. Adding a thin coating, laminate or adhesive can inhibit the braid elements from sliding with respect to each other, thereby locking the braid to a specific diameter. The coating can be applied while leaving the majority of the pores and pore area substantially open. Examples of thin coatings include urethanes and silicones with and without hydrophilic coatings and hydrophilic coatings with no tie layer.

Reducing the sliding friction of tractor to outer catheter wall, improving tractor to tip rolling, and/or enhancing tractor to inner catheter sliding may also be achieved by including a sliding skin or sleeve. For example, a thin (e.g., ultrathin) sleeve may be used. The sleeve would be made from low friction polymer (PET, PE, PP, PTFE, ePTFE, pebax, urethanes) by braiding, knitting, weaving, extrusion, melt blown, melt spinning, etc. The sleeve could be made from laser slotted tubing, chemical etching, micro machining. The sleeve could be also coated with a lubricious coating such as a hydrophilic coating. Lubricious coatings can be located on the outside and/or inside surfaces. The sleeve may be placed between the dozer element and the catheter wall and attached to the puller element. The sleeve may be less than 0.002" thick, ideally, less than 0.001" wall thickness. The sleeve may decouple the tractor clot grabbing system from the catheter wall, tip rolling and inner catheter dragging friction. The sleeve could be totally free from the tractor, connected to the tractor in discrete locations or connected fully to the tractor. This may allow the tractor to be designed to grab clot (larger wires: 0.001" to 0.002" for neuro, and 0.002" to 0.007" for other applications) and the skin to minimized in thickness and structure to reduce friction and skin bending stiffness.

In some variations, the tractor region may be formed of with a mixed or hybrid structure, combining one or more of interwoven or knitted braid polymer filaments with metallic filaments. The mixed structure (hybrid structure) may leverage both metallic elements interwoven with low friction polymer elements. The metallic filaments may create stiffness elements that may grip/grab a clot. The polymer filaments may aid in grabbing clot but may provide surface friction reduction to the outer catheter wall, the catheter tip and the inner catheter wall once around the tip.

Any of the apparatuses described herein may include a tractor having a hydrophilic/lubricous coating on the inside surface, e.g., for braided/knitted tractors, on the inside surface (contacting the outer and inner diameter of the catheter) of the braid/knit, which is in contact with the outside of the catheter. Examples of lubricous coatings include hydrophilic coatings (e.g., hydrogels) and hydrophobic coatings (e.g., fluorine coating such as PTFE & FEP, parylene, silicone, siloxane (silicone additive) added to various polymers including pebax to make any material more lubricious, Polyethylene, polypropylene, FEP)

As mentioned above, any of these apparatuses may include a distal tip that is less rigid (e.g., 'softer') than the more proximal regions of the distal tip. This may be achieved by having a structural supporting member reinforcing the distal tip, or by modifying the material forming the distal tip.

Any of the tractors described herein may include a marker or makers (e.g., radiopaque markers, such as gold, Pt, etc.).

Figure 2A:
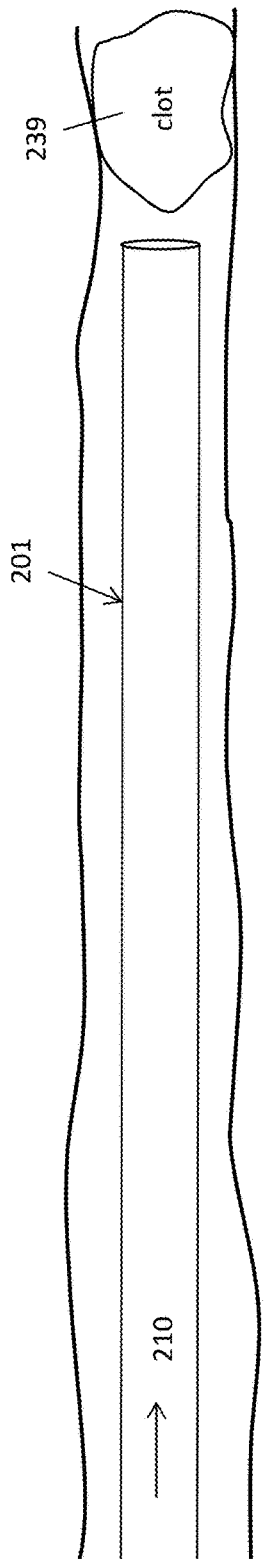
Figure 2B:
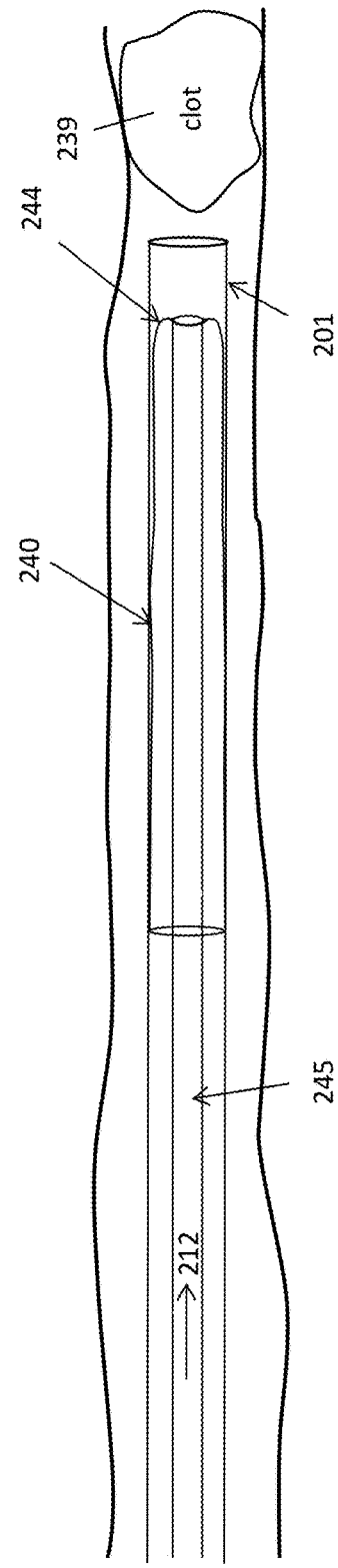
Figure 2C:
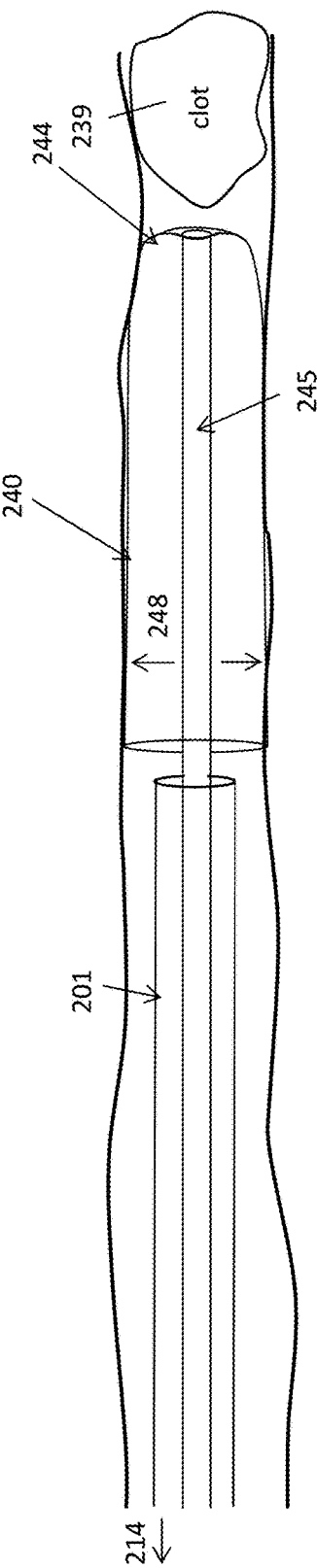

FIGS. 2A-2F illustrate an in situ method of deploying a mechanical thrombectomy apparatus. In FIG. 2A the elongate inversion support catheter 201 is positioned within the vessel, near a clot 239, e.g., by moving the elongate inversion support catheter distally 210 towards the clot. The elongate inversion support catheter may be positioned with a guidewire (not shown), or without a guidewire. The tractor assembly portion of the apparatus, e.g., a flexible tractor tube 244 and elongate puller 245 may be positioned with the catheter, or it may be moved through the catheter once it is in position within the vessel. In FIG. 2B, the tractor assembly 240 is positioned within the elongate inversion support catheter near the distal end. Once it is in an approximate location (e.g., near the clot 239), the flexible tractor tube 244 may be extended 212 from the distal end of the elongate inversion support catheter, as shown in FIG. 2C. The flexible tractor tube may be deployed out of the elongate inversion support catheter by pulling 214 the elongate inversion support catheter proximally and/or pushing the flexible tractor tube distally; once out of the elongate inversion support catheter, the flexible tractor tube is allowed to expand into a second (expanded configuration) outside of the elongate inversion support catheter. As mentioned, the flexible tractor tube may be biased so that in this un-inverted configuration the diameter of the flexible tractor tube is between 1.1× and 5× the OD of the elongate inversion support catheter (e.g., typically between 1.1× and 3× the OD of the elongate inversion support catheter, etc.). The elongate inversion support catheter may then be moved back distally, between the flexible tractor tube 244 and the elongate puller 245, as shown in FIG. 2D.

In practice, the catheter must fit into the open (free) end of the flexible tractor portion. The apparatus may be modified, e.g., by including an annular bias at or near the open end of the flexible tractor portion. Alternatively or additionally, the open end may be biased (e.g., heat set, shape set, etc.) to invert over or under itself.

In FIG. 2E, once the elongate inversion support catheter is positioned distally between the flexible tractor tube and elongate puller, the flexible tractor tube may be rolled and inverted 266 into the elongate inversion support catheter, as shown in FIG. 2F. In this example, the elongate puller 245 may be pulled through the elongate inversion support catheter proximally 218 to pull the flexible tractor tube proximally into the elongate inversion support catheter. In FIG. 2F, the rolling tractor is shown grabbing the clot 239, and inverting into the elongate inversion support catheter while pulling the clot into the elongate inversion support catheter. The flexible tractor tube in this example is biased to expand to between 1.1 and 4 times an outer diameter of the elongate inversion support catheter in an un-inverted configuration (e.g., FIG. 2D) and is further biased to expand to greater than 0.5× an inner diameter of the elongate inversion support catheter in an inverted configuration (when drawn into the catheter as shown in FIG. 2F).

FIGS. 3A-3B illustrate another example of a tractor assembly including a flexible tractor tube 344 attached at one end to an elongate puller 345. In this example, similar to FIG. 1I, the elongate puller has a stepped profile. The narrower-diameter region formed in the elongate puller by the stepped profile may allow the flexible tractor tube of the tractor assembly 334 to be compressed with a smaller profile within the elongate inversion support catheter. In FIG. 3A the flexible tractor tube 344 is shown collapsed (compressed) against the elongate puller. This configuration may provide improved mobility within the elongate inversion support catheter. This variation may also be readily adapted for application to a vacuum through the hollow elongate puller. In FIG. 3A the flexible tractor tube is shown as compressed or collapsed. FIG. 3B shows the flexible tractor tube in an expanded configuration. In this example, the flexible tractor tube 244 is expanded outward from the puller. The tractor tube may be biased (e.g., heat set, shape set, etc.) in this configuration. Alternatively or additionally, the apparatus may be compressed and held within an elongate inversion support catheter.

Figure 4A:
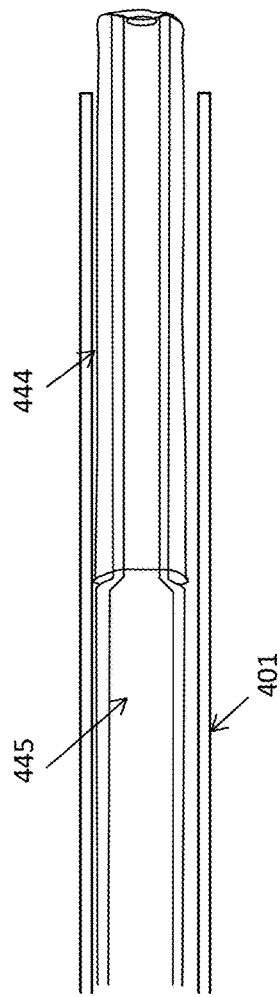
FIGS. 4A-4C illustrate deployment of the elongate puller with a stepped outer diameter shown in FIGS. 3A-3B.
Figure 4B:
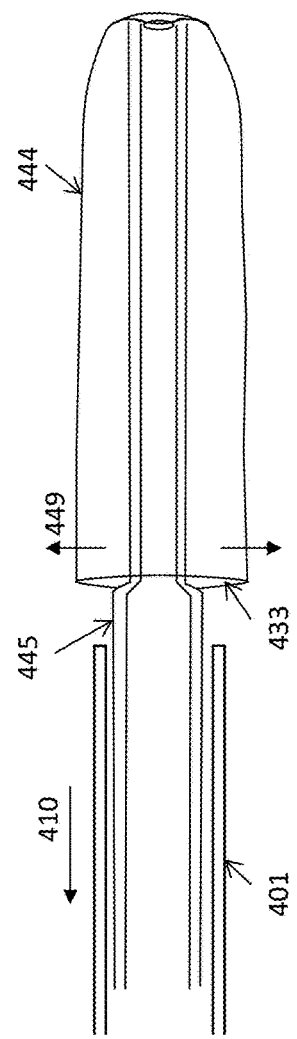
Figure 4C:
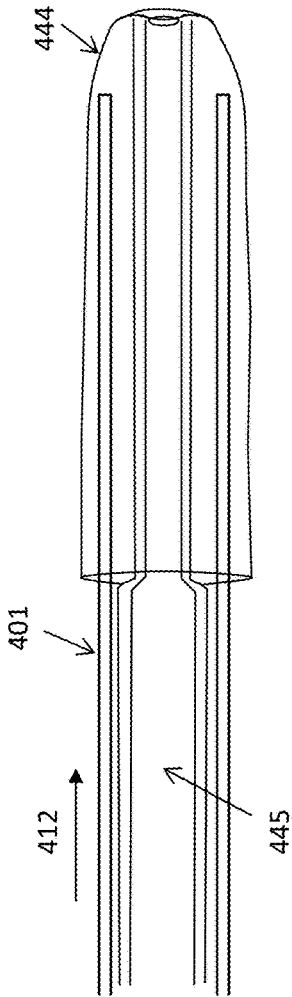

FIGS. 4A-4C illustrate deployment of the elongate puller with a stepped outer diameter, such as the variation shown in FIGS. 3A-3B, from a delivery configuration to a deployed configuration. In FIG. 4A the elongate puller 445 is positioned at the distal end of the elongate inversion support catheter 401; the flexible tractor tube 444 is attached at one end to the puller. In FIG. 4B, the flexible tractor tube 444 is extended from the distal end opening of the elongate inversion support catheter and expanded 449 at least slightly. In this example, the elongate inversion support catheter 401 may be withdrawn proximally 410. An annular bias, described in greater detail below, may be used in this variation as well, to hold the free, open end 433 of the tractor tube 444 open. As shown in FIG. 4C, the elongate inversion support catheter 401 may then be positioned 412 between the flexible tractor tube 444 and the elongate puller 445, so that the elongate inversion support catheter 401 can support the flexible tractor tube a the distal end so that it can roll and invert into the elongate inversion support catheter, e.g., by pulling the elongate puller to invert into the elongate inversion support catheter.

Figure 5A:
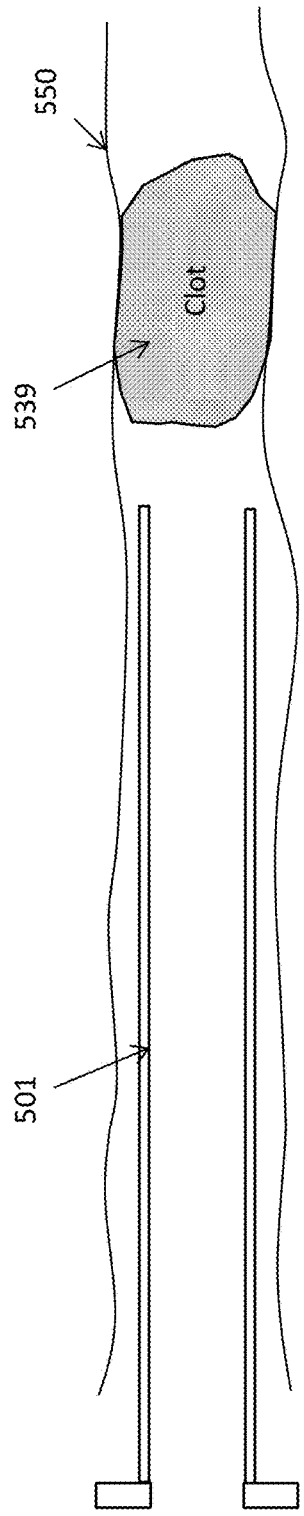
FIG. 5A-5F illustrate the use of the apparatus of FIG. 3A-3B, including an annular bias, to remove a thrombus (clot) from within a vessel.
Figure 5B:
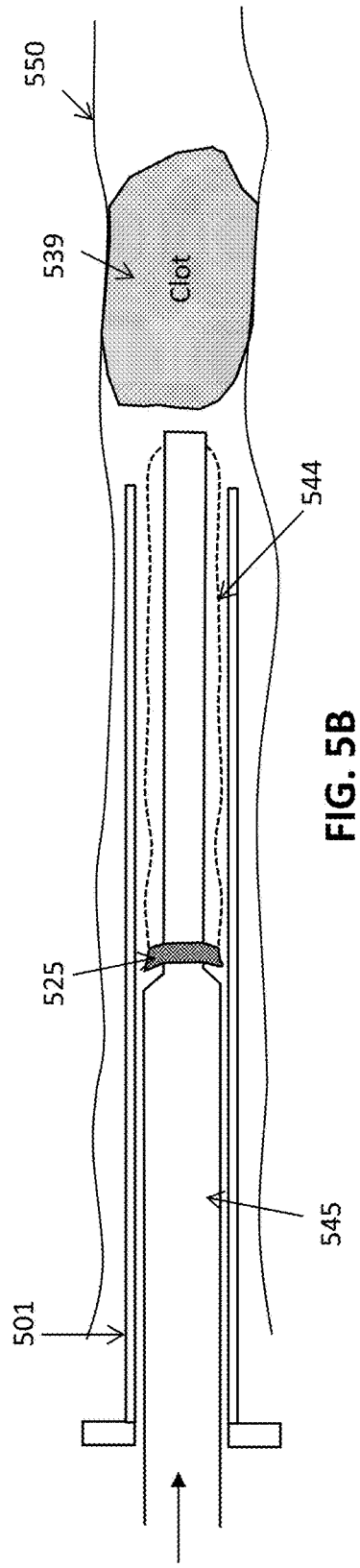
Figure 5C:
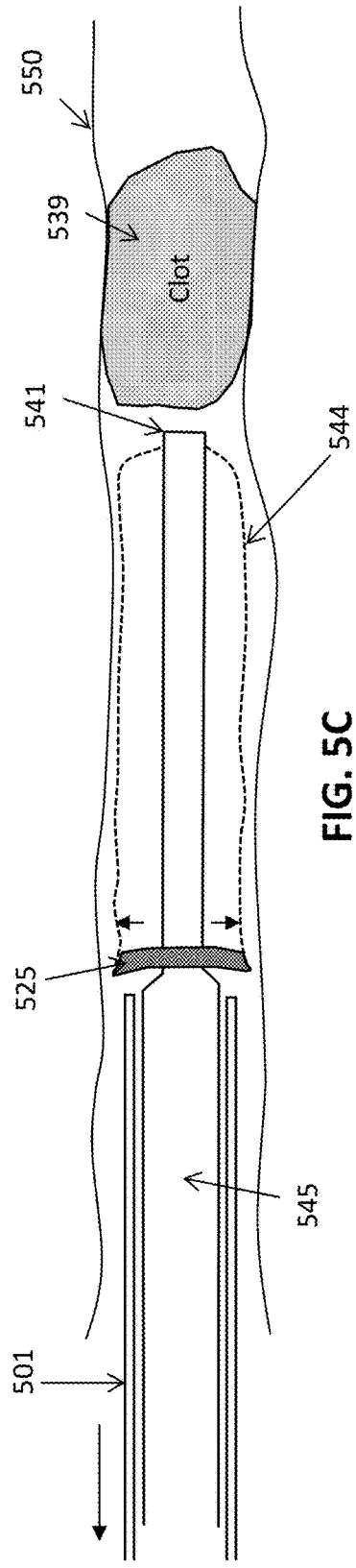
Figure 5D:
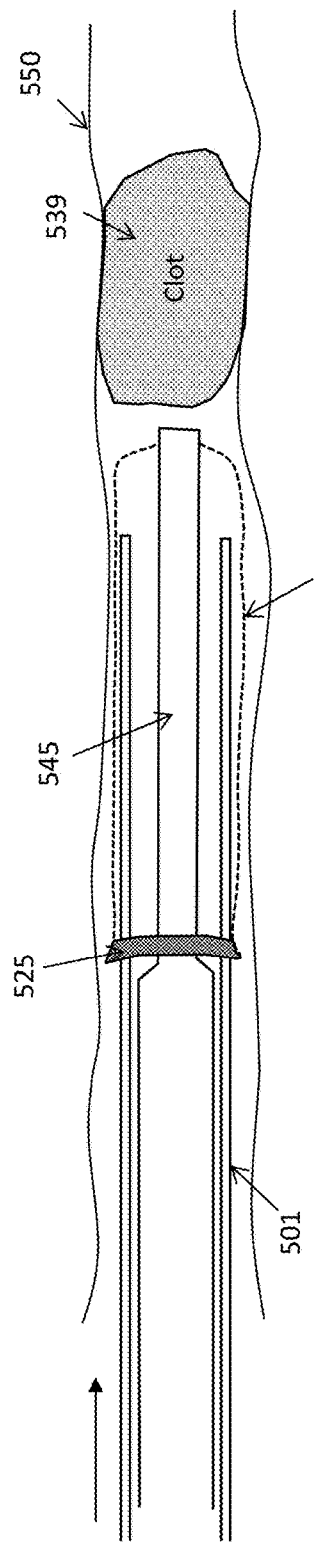
Figure 5E:
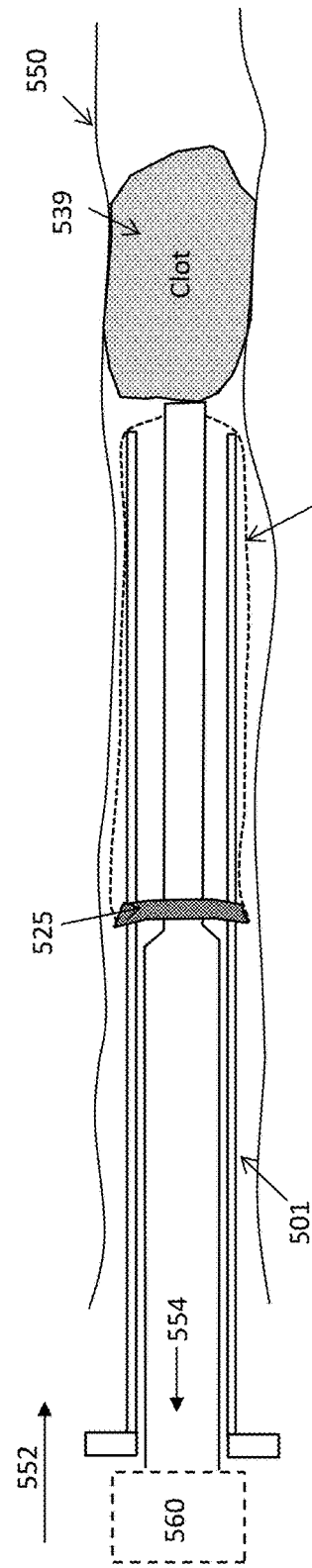
Figure 5F:
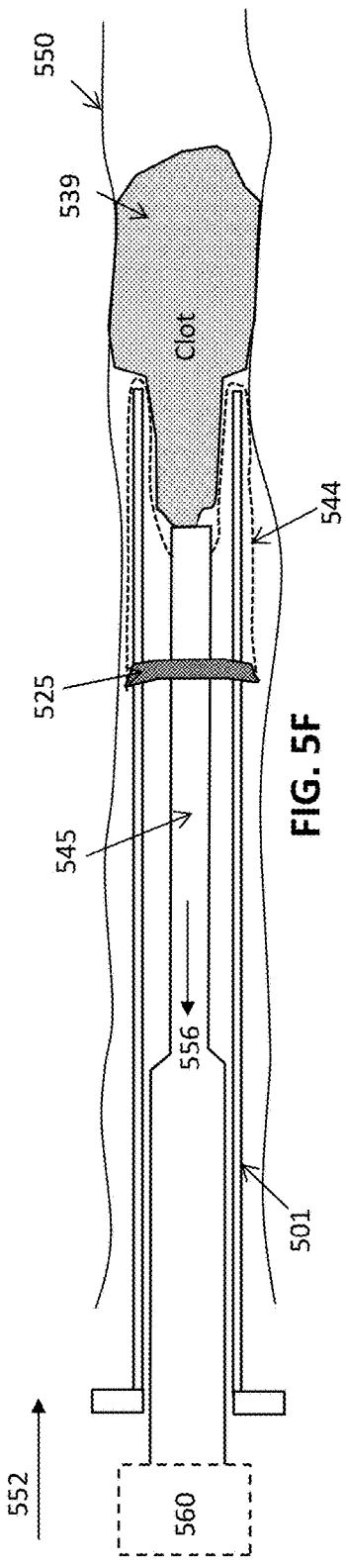

FIG. 5A-5F illustrate the use of the apparatus of FIGS. 3A-3B, including an annular bias, to remove a thrombus (clot) from within a vessel. In FIG. 5A the elongate inversion support catheter 501 is positioned near a clot 539 in the vessel 550. The elongate pusher 545, to which a flexible tractor tube 544 is attached, forming a tractor assembly, may be positioned in the elongate inversion support catheter at the distal end. In FIG. 5B the elongate pusher is attached to the first end of the tractor tube 544 at a first end, with an annular bias open and unsecured (e.g., free) at the second end. The second, open or free end 533 may include one or more annular biases 525 that may is extended distally through the catheter and out of the distal end of the elongate inversion support catheter 501, as shown in FIG. 5B. In FIG. 5C, the annular bias 525 holds the free end 533 of the flexible tractor tube open. Alternatively or additionally, the flexible tractor tube may be biased to expand to diameter that is slightly greater than the outer diameter of the catheter 501 (e.g., greater than 1.1× the outer diameter of the elongate inversion support catheter), however the annular bias 525 may be open even slightly more, and may be stiffer (e.g., more rigid) when expanded open, as shown in FIG. 5C. The elongate inversion support catheter 501 may then be inserted distally through the annular bias 525 and between the flexible tractor tube 544 and the elongate puller 545, as shown in FIGS. 5D-5E. The entire apparatus may be advanced distally 552, either before or while rolling the tractor into the elongate inversion support catheter 501. A vacuum 560 (optional) may be applied through the elongate puller 544 and/or elongate inversion support catheter and/or the puller may be drawn proximally 554, as shown in FIG. 5E. In FIG. 5F, withdrawing 556 the elongate puller proximally (with or without a vacuum) to roll the flexible tractor over the distal end of the elongate inversion support catheter so that it inverts into the elongate inversion support catheter may draw the clot into the elongate inversion support catheter, as shown.

The variations shown in FIGS. 3A-3B, 4A-4C and 5A-5F having a stepped outer diameter in the puller may maximize the inner diameter of the tractor assembly, which may aid in aspiration (mechanical or by vacuum). In any of these variations, a vacuum can be applied to the apparatus (e.g., the tractor assembly) and/or the elongate inversion support catheter. In some variations the OD of the puller along at least part of its length (e.g., proximal to the free end of the tractor tube) may be approximately the same as the ID of the elongate inversion support catheter. This may aid in forming a seal such that vacuum applied through the elongate puller may be maintained the distal end of the elongate inversion support catheter and/or puller, which may help in grabbing the clot.

Figure 6A:
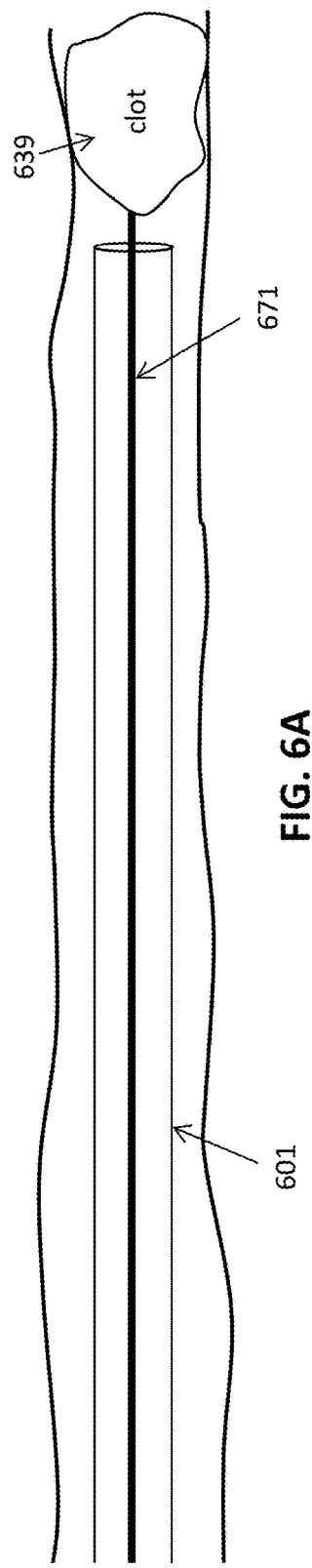
Figure 6B:
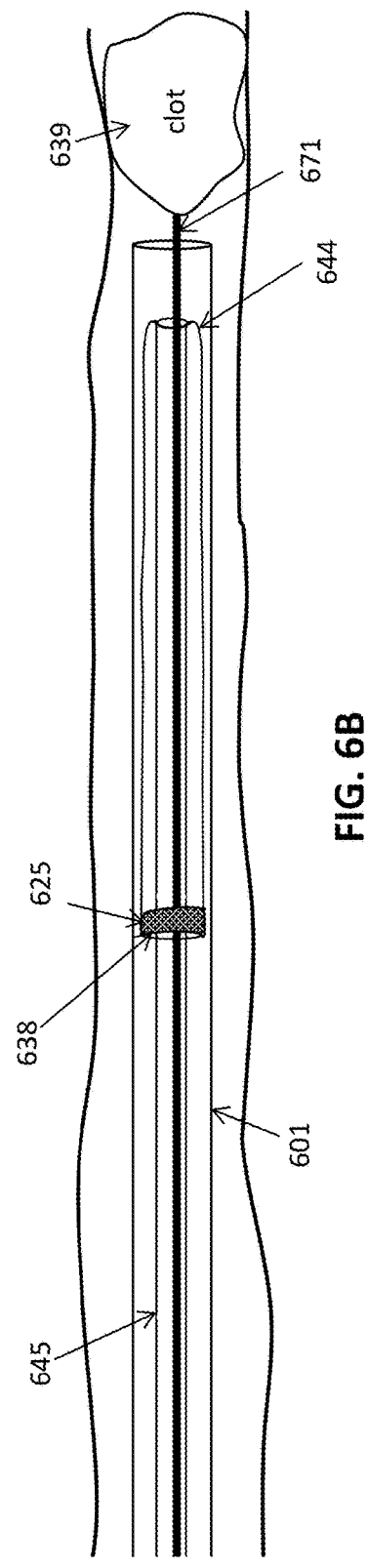
Figure 6C:
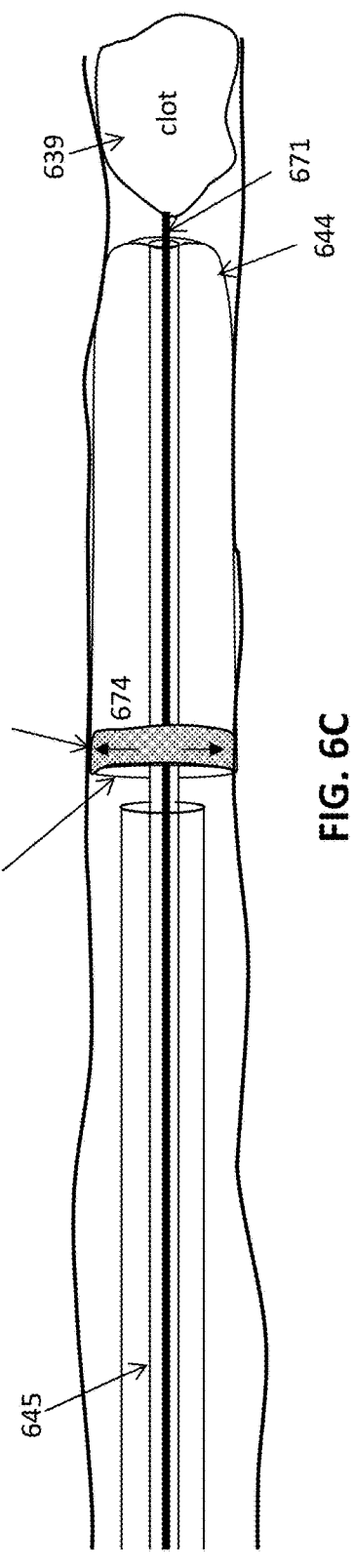

FIGS. 6A-6F illustrate another variation of an apparatus including an annular bias 625 on an open, free, end 638 of the flexible tractor tube 644. In FIG. 6A, the elongate inversion support catheter 601 is positioned in the vessel. In FIG. 6A, a guidewire 671 is shown. The catheter may be advanced over the guidewire, to approach the clot 639. In FIG. 6B, the elongate puller 645 and flexible tractor tube 644 are positioned distally within the elongate inversion support catheter 601, also over the guidewire 671. The tractor assembly includes the flexible tractor tube 644 attached at one end to the elongate puller 645, with the other end of the flexible tractor tube open and free (e.g., not attached to the puller or catheter), but coupled to an annular bias 625. The guidewire 671 may be removed or left in position when deploying the flexible tractor tube from the distal end of the elongate inversion support catheter. In FIG. 6C, the tractor assembly, including the distal end of the elongate puller 645 and the entire flexible tractor tube 644 is extended distally from the elongate inversion support catheter 601. The annular bias 625 expands 674 to a diameter that is greater than the outer diameter of the elongate inversion support catheter 601 (e.g., greater than 1.1× the diameter of the elongate inversion support catheter). The annular bias may also act to stiffen or otherwise stabilize this end region of the tractor tube (which may be on or near the open end of the tractor tube) so that the elongate inversion support catheter 601 can be inserted through the annular bias, as shown in FIG. 6D.

In FIGS. 6D and 6E, the elongate inversion support catheter 601 is advanced distally 671 within the annular bias and between the flexible tractor tube 644 and the elongate puller 645, so that the elongate inversion support catheter can support the flexible tractor tube 644 as it is pulled 678 proximally by the elongate puller 645 to roll 663 and invert over the distal end opening of the elongate inversion support catheter (as shown in FIG. 6F). The apparatus may be advanced (e.g., while pulling the elongate puller proximally) to grab and remove a clot 639 from the vessel, as shown in FIG. 6E.

In any of these variations, the annular bias may be configured to keep the free end of the tractor tube open when deployed. The annular bias may be welded braided, bonded, glued and/or integral to the tractor tube. The annular bias may be attached to an outside, an inside or both (e.g., may be folded over the open end of the tractor tube, or may be attached on either side of the tractor tube.

Figure 7:
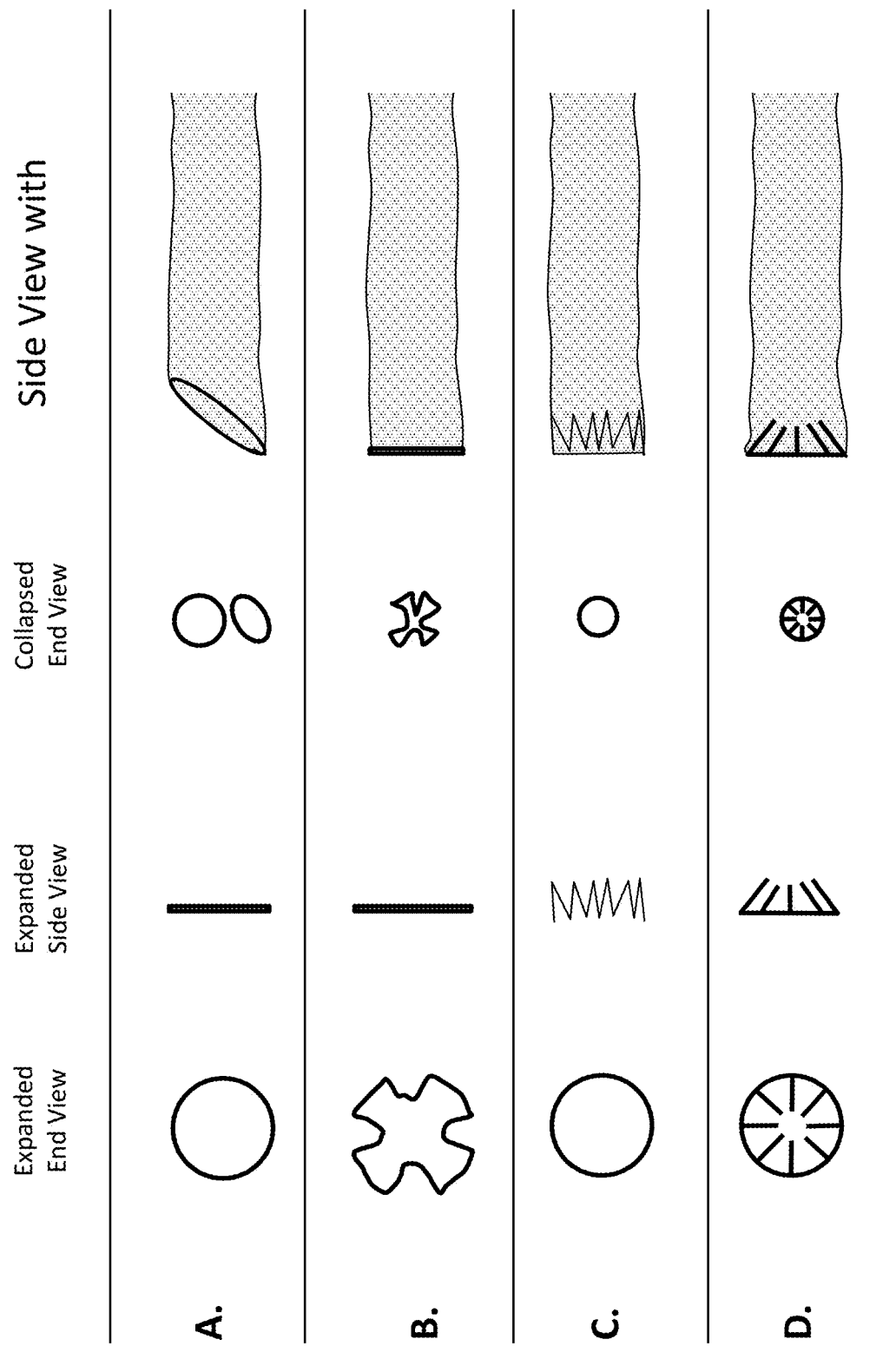
FIGS. 7A-7D illustrate four variations of annular biases that may be used to support the expanded open (free) end of the flexible tractor tube in any of the variations described herein. The vertical columns illustrate an expanded end view, an expanded side view, a collapsed end view (e.g., within the elongate inversion support catheter) and a side view shown attached to a flexible tractor tube, respectively, from left to right.

FIGS. 7A-7D illustrate four variations of annular biases that may be used to support the expanded open (free) end of the flexible tractor tube in any of the variations described herein. For example, FIG. 7A shows an annular bias forming a circular loop in the expanded end view. The loop may be formed of a shape memory material, such as Nitinol, or a polymeric material. The loop may be orthogonal to the braid or weave of the tractor tube, which may aid in compressing when rolling over the distal end opening of the elongate inversion support catheter. In some variations the annular bias may be heat set to an irregular circular shape to aid in folding or may include buckling points around the perimeter of the annular bias. In the side view shown of the annular bias of FIG. 7A the annular bias is angled relative to the long axis of the tractor tube; alternatively, the annular bias may be attached perpendicular to the long axis (similar to FIG. 7B.

In any of the variations described herein, the annular bias may be configured to include one or more predetermined collapse/expansion locations about which the annular bias is configured to collapse or expand as it transitions between an expanded and a collapsed configuration. For example, the predetermined locations may be defined by the one or more lobes or vertices forming the annular bias. FIG. 7B shows an example in which the annular bias includes folds or bends that may control the collapsed configuration. In this example, the annular bias has lobes or petals, which may predictably collapse when compressed (e.g., see the collapsed end view). The annular bias may be shaped to compress into a small diameter as the tractor tube rolls around the tip of the elongate inversion support catheter. The u-shaped features (lobes, petals, etc.) at noon, 3 o'clock, 6 o'clock, and 9 o'clock are one example. Other examples include the use of fewer (e.g., 2 lobes, 3 lobes) or more (e.g., 5 lobes, 6 lobes, etc.).

In general, the annular bias has a stiffness that is greater than the stiffness of the flexible tractor tube (e.g., greater than 1.5× the stiffness, greater than 2× the stiffness, etc.).

In FIG. 7C the annular bias is a stent-like structure having a plurality of zig-zagging struts (members). The stent-like annular bias may easily invert when rolling around the catheter tip. The length of the zig-zags may be limited to <about 5-10 mm. In some variation multiple rows of zig-zags may be used.

FIG. 7D shows an example of an annular bias that is funnel-shaped. In operation, this structure may both help the insertion of the elongate inversion support catheter between the tractor tube and the elongate puller, and may also help with inverting the end of the tractor tube and pulling it into the elongate inversion support catheter.

An example of a stent-like annular bias is shown in FIGS. 8A-8C. In this example the annular bias is formed of a sinusoidally arranged loop of wire (though multiple wires/struts may be used) having a 0.002" thickness, which is attached to the open end region of a 144 end 0.00075" NiTi braid flexible tractor tube. FIG. 8A shows the expanded annular bias 803, shown attached to a flexible tractor tube 801 in FIG. 8B. The flexible tractor tube 801 with the annular bias 803 of FIG. 8A is shown attached to an elongate puller 805 in FIG. 8C. In the example shown in FIG. 8, the annular bias is attached near the open (free) end of the tractor tube at the distal end region, but is slightly distal to the end. In some variations the annular bias is attached at the very end (or edge) of the open end of the flexible tractor tube.

Any of the annular biases described herein may also be configured to enhance rolling of the distal end of the apparatus over the tip of the elongate inversion support catheter. For example, FIG. 9A shows another example of a flexible tractor tube (144 end 0.00075" NiTi) having an annular bias, being rolled 961 into the elongate inversion support catheter by pulling proximally on the tractor tube. In FIG. 9B the open end of the flexile tractor tube (with an attached sent-like annular bias 903) is shown rolling over the open distal end of the elongate inversion support catheter. In order to enhance this rolling, in some variations, the annular bias may also include one or more extension (e.g., lead in arms) that may extend along the long axis (length) of the flexible tractor tube. A schematic of this configuration is shown in FIG. 9C. In FIG. 9C the stent-like annular bias includes lead-in arms that may help it roll over the elongate inversion support catheter. The lead-in arms may help the annular bias to roll around the catheter tip and into the ID of the elongate inversion support catheter. One or more (e.g., 1, 2, 3, 4, 5, 6, 7, 8, etc.) lead-in arms may be used; these lead in arms may be all the same length of different lengths.

Figure 10:
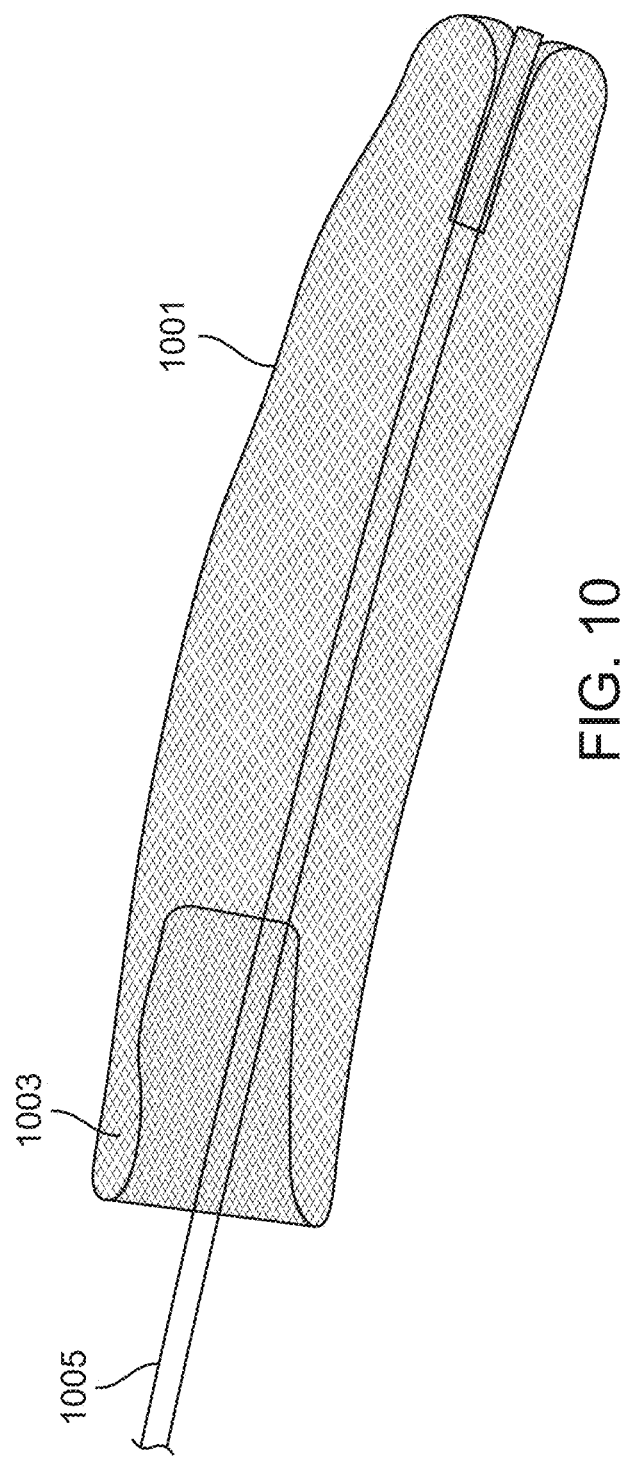
FIG. 10 illustrates an example of a flexible tractor tube that is heat-set at the open end to have an inverted shape to allow for ease of insertion of the elongate inversion support catheter.

FIG. 10 illustrates an example of a flexible tractor tube 1001 that is heat-set at the open end to have an inverted shape 1003 to allow for ease of insertion of the elongate inversion support catheter. In FIG. 10, the open (loose) end of the flexible tractor tube folds back under itself which may help guide the elongate inversion support catheter into the space between the flexible tractor tube 1001 and the elongate puller 1005. In this example, the flexible tractor tube may not require an additional annular bias.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A mechanical thrombectomy apparatus for removing a clot from a vessel, the apparatus comprising:
   an elongate inversion support catheter having a distal end and a distal end opening;
   an elongate puller extending within the elongate inversion support catheter;
   a flexible tractor tube having a free first end and a second end that is coupled to a distal end region of the elongate puller, wherein the flexible tractor tube is inverted over the elongate puller and is held within the elongate inversion support catheter in a collapsed first configuration; and
   an annular bias disposed at least partially around the free first end of the flexible tractor tube,
   wherein the flexible tractor tube is configured to be extended from the distal end opening of the elongate inversion support catheter and to expand into an expanded second configuration, and
   wherein the annular bias has a diameter that is larger than an outer diameter of the elongate inversion support catheter when the flexible tractor tube is in the expanded second configuration.

2. The apparatus of claim 1, wherein the annular bias comprises a ring.

3. The apparatus of claim 1, wherein the annular bias comprises a stent having a zig-zag strut pattern.

4. The apparatus of claim 1, wherein the annular bias has a diameter that is between 1.1× and 5× of the outer diameter of the elongate inversion support catheter when the flexible tractor tube is in the expanded second configuration.

5. The apparatus of claim 1, wherein the annular bias comprises a plurality of predetermined collapse locations about which the annular bias is configured to collapse or expand.

6. The apparatus of claim 1, wherein the annular bias comprises a plurality of lobes, wherein the plurality of lobes comprise a respective plurality of collapse locations on the annular bias.

7. The apparatus of claim 1, wherein the annular bias is coupled to one or more of an inner side and an outer sidediameter of the flexible tractor tube.

8. The apparatus of claim 1, wherein the annular bias comprises a plurality of lead-in arms oriented along a long axis of the flexible tractor tube.

9. The apparatus of claim 1, further wherein the flexible tractor tube in an un-inverted configuration is biased to expand to between 1.1 and 4 times an outer diameter of the elongate inversion support catheter and wherein the flexible tractor tube is further biased in an inverted configuration to expand to greater than 0.5× an inner diameter of the elongate inversion support catheter.

10. The apparatus of claim 1, wherein the elongate inversion support catheter is configured to be pushed through the annular bias and between the flexible tractor tube and an outer wall of the elongate puller when the flexible tractor tube is in the expanded second configuration.

11. The apparatus of claim 1, wherein the flexible tractor tube comprises a woven, braided, mesh or knitted material.

12. The apparatus of claim 1, wherein the flexible tractor tube is sufficiently soft so as to collapse radially under an axial compression of less than 200 g of force.

13. The apparatus of claim 1, further comprising a guidewire lumen extending through the elongate puller, the guidewire lumen being configured to allow passage of a guidewire therethrough.

14. The apparatus of claim 1, wherein the flexible tractor tube is knitted.

15. The apparatus of claim 1, wherein the flexible tractor tube comprises one or more of steel, polyester, nylon, expanded Polytetrafluoroethylene (ePTFE), Nitinol, and a fabric.

16. The apparatus of claim 1, wherein a material hardness of the elongate inversion support catheter decreases along a length of the distal end thereof, wherein the distal end opening has a material hardness that is greater than a material hardness of a region immediately proximal to the distal end, and wherein the distal end opening has a rounded lip profile.

17. The apparatus of claim 1, wherein the elongate puller comprises a hypotube.

18. The apparatus of claim 1, wherein the flexible tractor tube has a length between 3 cm to 50 cm.

19. A mechanical thrombectomy apparatus for removing a clot from a vessel, the apparatus comprising:
    an elongate inversion support catheter having a distal end and a distal end opening;
    an elongate puller extending within the elongate inversion support catheter, wherein the elongate puller comprises a central lumen;
    a flexible tractor tube having a free first end and a second end that is coupled to a distal end region of the elongate puller, wherein the flexible tractor tube comprises a woven, braided, mesh and/or knitted material, is inverted over the elongate puller, and is held within the elongate inversion support catheter in a collapsed first configuration, and wherein the flexible tractor tube is biased in an un-inverted configuration to expand to between 1.1 and 4 times an outer diameter of the elongate inversion support catheter in and is further biased in an inverted configuration to expand to greater than 0.5× an inner diameter of the elongate inversion support catheter; and
    an annular bias disposed at least partially around the free first end of the flexible tractor tube, wherein the flexible tractor tube is configured to be extended from the distal end opening of the elongate inversion support catheter and to expand into an expanded second configuration, wherein the annular bias has a diameter that is larger than an outer diameter of the elongate inversion support catheter in the expanded second configuration so that the elongate inversion support catheter may be pushed through the annular bias and between the flexible tractor tube and an outer wall of the elongate puller.

20. A method of deploying a mechanical thrombectomy apparatus for removing a clot from a vessel, the method comprising:
    positioning an elongate inversion support catheter within a lumen of the vessel;
    extending an elongate puller and a flexible tractor tube out of a distal end of the elongate inversion support catheter, wherein the flexible tractor tube has a free first end coupled to an annular bias and a second end that is coupled to a distal end region of the elongate puller, so that the flexible tractor tube expands from a collapsed first configuration within the elongate inversion support catheter into an expanded second configuration, and wherein the annular bias holds the flexible tractor tube open to a diameter that is larger than an outer diameter of the elongate inversion support catheter when the flexible tractor tube is in the expanded second configuration;
    advancing the elongate inversion support catheter distally through the annular bias and between the flexible tractor tube and the elongate puller; and
    pulling the elongate puller proximally to roll the flexible tractor tube over a distal end opening of the elongate inversion support catheter so that the flexible tractor tube inverts into the elongate inversion support catheter, wherein the flexible tractor tube is biased in an un-inverted configuration to expand to between 1.1 and 4 times an outer diameter of the elongate inversion support catheter and is further biased in an inverted configuration to expand to greater than 0.5× an inner diameter of the elongate inversion support catheter within the elongate inversion support catheter.

21. The method of claim 20, further comprising retrieving a clot from within the vessel into the elongate inversion support catheter by rolling the flexible tractor tube over the distal end opening.

22. The method of claim 20, wherein positioning the elongate inversion support catheter within the lumen of the vessel comprises extending the elongate inversion support catheter over a guidewire.

23. The method of claim 20, wherein extending the elongate puller and the flexible tractor tube out of the distal end of the elongate inversion support catheter comprises pushing the elongate puller distally out of the elongate inversion support catheter.

24. The method of claim 20, wherein extending the elongate puller and the flexible tractor tube out of the distal end of the elongate inversion support catheter comprises expanding the annular bias, and wherein the annular bias comprises a stent coupled to the free first end of the flexible tractor tube.

25. The method of claim 20, wherein extending the elongate puller and the flexible tractor tube out of the distal end opening of the elongate inversion support catheter comprises extending a woven, braided, mesh and/or knitted material forming the flexible tractor tube out of the distal end opening of the elongate inversion support catheter.

26. The method of claim 20, further comprising supporting the flexible tractor tube over the distal end opening so that the flexible tractor rube does not radially collapse under axial compression, wherein the flexible tractor tube is sufficiently soft such that without support it collapses radially under an axial compression of less than 200 g of force.

* * * * *